(12) United States Patent
Tinker

(10) Patent No.: US 8,911,748 B2
(45) Date of Patent: Dec. 16, 2014

(54) CHOLERA TOXIN CHIMERA AND ITS USE AS A STAPH VACCINE

(71) Applicant: Boise State University, Boise, ID (US)

(72) Inventor: Juliette Tinker, Eagle, ID (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 13/896,854

(22) Filed: May 17, 2013

(65) Prior Publication Data

US 2013/0266607 A1 Oct. 10, 2013

Related U.S. Application Data

(63) Continuation-in-part of application No. 13/328,686, filed on Dec. 16, 2011.

(51) Int. Cl.
| | |
|---|---|
| *A61K 39/085* | (2006.01) |
| *A61K 39/00* | (2006.01) |
| *A61K 39/02* | (2006.01) |
| *A61K 45/00* | (2006.01) |
| *A61K 38/00* | (2006.01) |
| *C07K 1/00* | (2006.01) |
| *A61K 39/39* | (2006.01) |
| *C07K 14/31* | (2006.01) |
| *C07K 14/28* | (2006.01) |

(52) U.S. Cl.
CPC .............. *A61K 39/39* (2013.01); *A61K 39/085* (2013.01); *C07K 14/31* (2013.01); *C07K 14/28* (2013.01); *Y10S 424/823* (2013.01); *Y10S 424/828* (2013.01); *Y10S 424/829* (2013.01); *Y10S 530/825* (2013.01)
USPC ................ 424/243.1; 424/234.1; 424/192.1; 424/190.1; 424/184.1; 424/236.1; 424/278.1; 424/261.1; 424/823; 424/828; 424/829; 514/1.1; 530/350; 530/300; 530/825

(58) Field of Classification Search
None
See application file for complete search history.

(56) References Cited

U.S. PATENT DOCUMENTS

2003/0187225 A1* 10/2003 Penichet et al. .............. 530/351
2013/0156802 A1    6/2013 Tinker

OTHER PUBLICATIONS

Challa et al. Adv. Virol. Article ID 713769, pp. 1-11, ePub Sep. 22, 2011.*
Burman et al. (J. Virol. 80: 9798-9810, 2006.*

* cited by examiner

*Primary Examiner* — S. Devi
(74) *Attorney, Agent, or Firm* — McKee, Voorhees & Sease

(57) ABSTRACT

The present invention relates to chimeric protein vaccines and methods of use thereof in the treatment of *Staphylococcus aureus*. One embodiment of the present invention provides a method of generating an immune response in a mammal, that includes administering to the mammal, a composition having a chimeric protein having at least one of: a portion of a cholera toxin, a portion of a heat-labile toxin, and a portion of a shiga toxin; and an antigen having at least one of: an antigenic material from *S. aureus* and an antigenic material from a *S. aureus*-specific polypeptide.

7 Claims, 15 Drawing Sheets

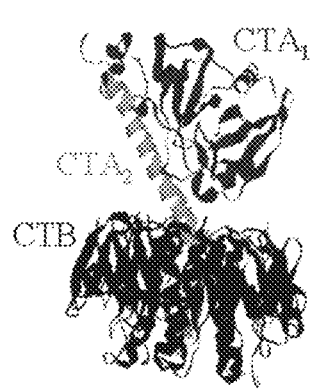 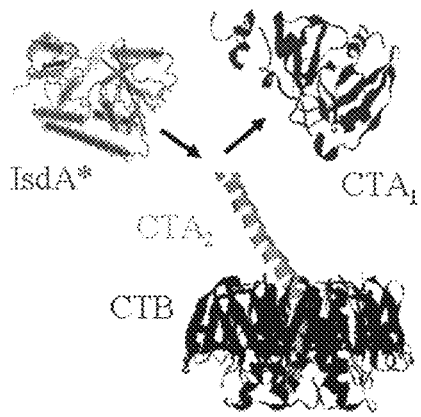 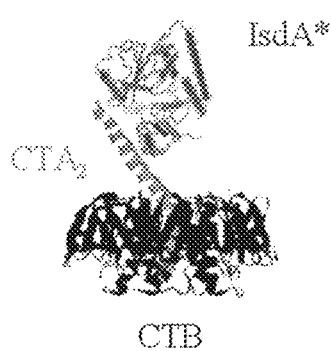
FIG. 1A　　　　　FIG. 1B　　　　　FIG. 1C
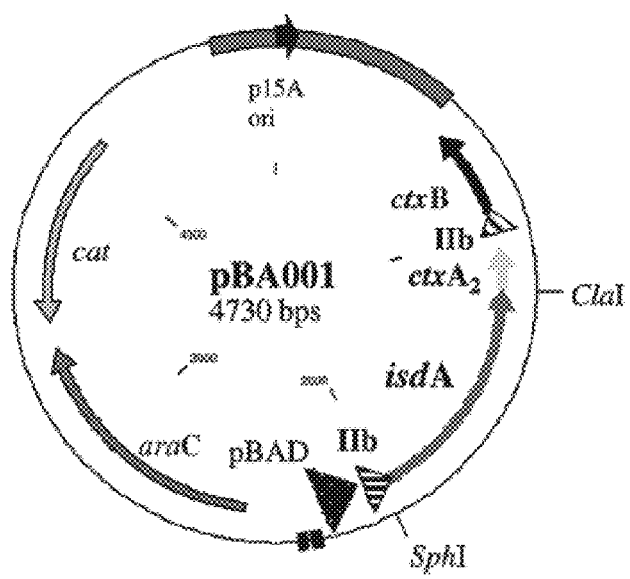
FIG. 2

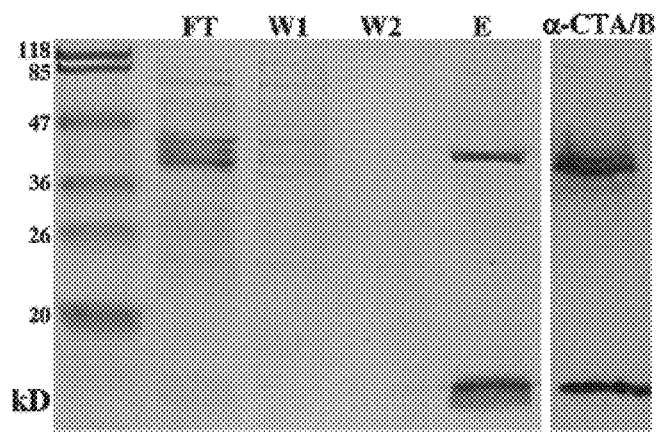
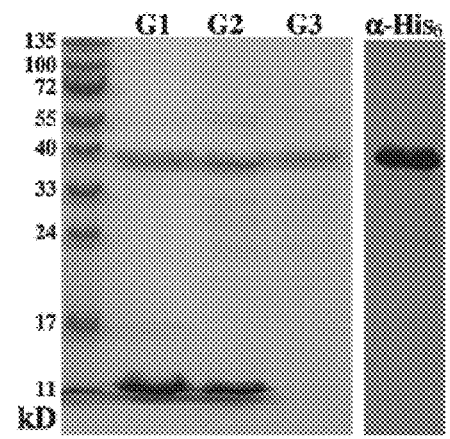
FIG. 3A    FIG. 3B
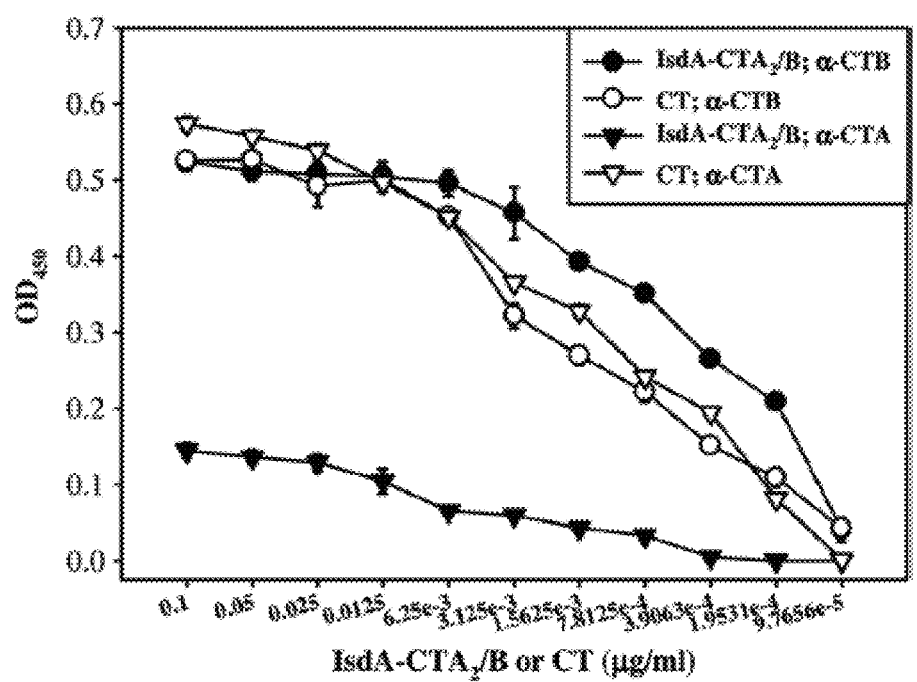
FIG. 4

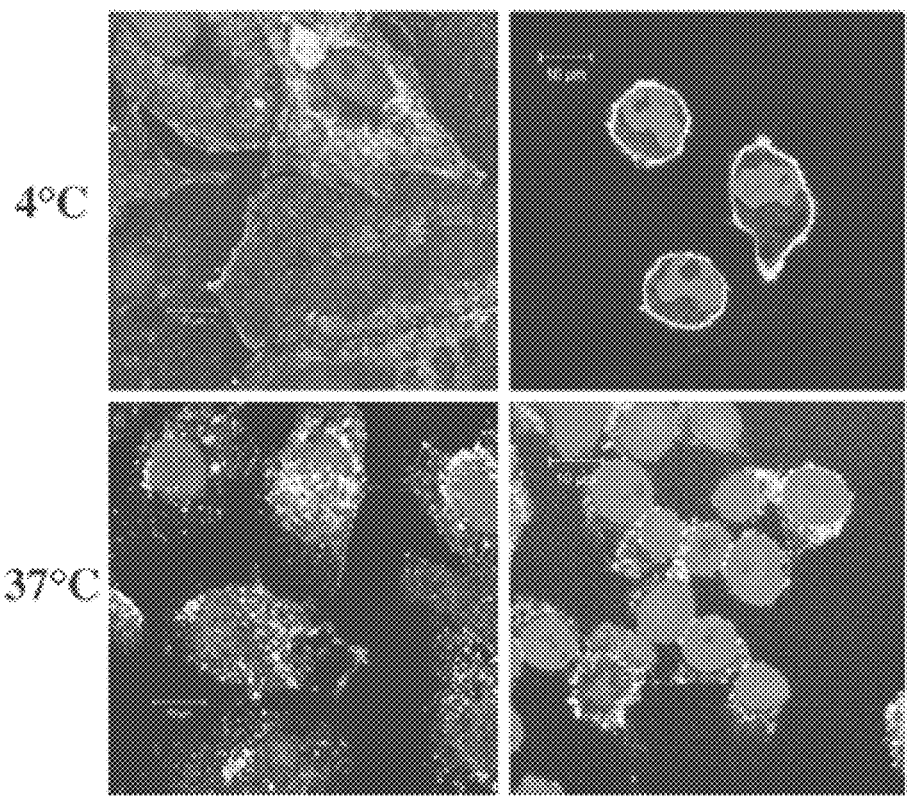
FIG. 5A  FIG. 5C
4°C
37°C
FIG. 5B  FIG. 5D
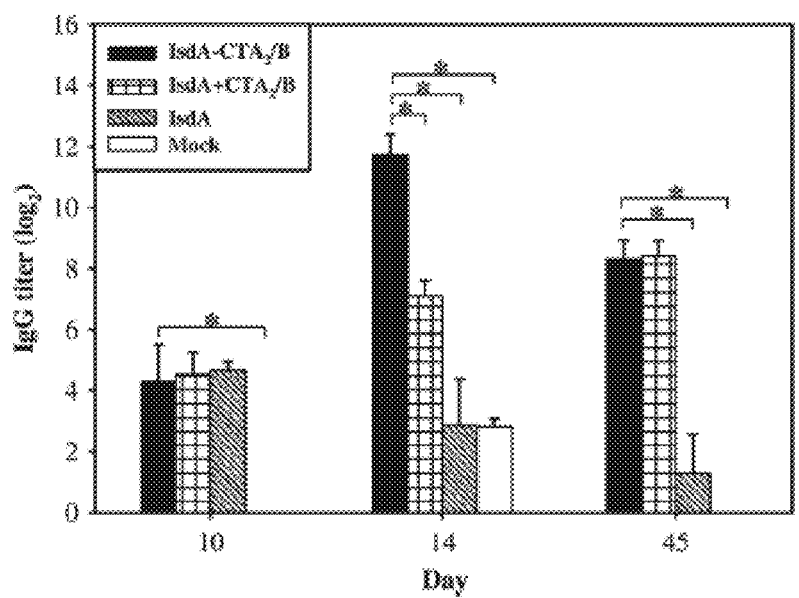
FIG. 6

CHOLERA TOXIN CHIMERA AND ITS USE AS A STAPH VACCINE

RELATED APPLICATION

This application is a continuation-in-part of U.S. patent application Ser. No. 13/328,686, filed on Dec. 16, 2011, pending. The entire teachings of the above application are incorporated herein by reference.

FEDERAL FUNDING LEGEND

This invention was supported in part with government support under USDA CREES Seed Grant #2009-01778, 2008 WWAMI ITHS Small Project Grant #3872, 2012 ITHS Small Project Grant #5617, NIH Grant #P20 RR016454 from INBRE Program of the National Center for Research Resources, and a 2012 Idaho SBOE grant #IF-13-006 The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 17, 2013, is named 083956-0028_SL.txt and is 53,242 bytes in size.

BACKGROUND

The present invention relates to infectious diseases and, more particularly, to chimeric protein vaccines and methods of use thereof in the treatment of *Staphylococcus aureus*.

*Staphylococcus aureus* (*S. aureus*) is a common cause of hospital-acquired infections and represents an important public health threat. *S. aureus* can cause nosocomial (hospital) and community-acquired infections including impetigo, cellulitis, food poisoning, toxic shock syndrome, invasive necrotizing pneumonia, and endocarditis. *S. aureus* is also the most common species of staphylococci to cause Staph infections. Currently, it is one of the top causes of infectious disease deaths in the United States.

*S. aureus* also causes mastitis, which is a major problem in dairy cows with considerable economic implications. For example, contagious mastitis in dairy cows is most commonly caused by *S. aureus* and is one of the most common diseases infecting dairy cattle in the United States. *S. aureus* causes a persistent, inflammatory reaction of the udder tissue that can lead to chronic infections that result in the cow being culled from the herd. Milk from cows with mastitis also typically has higher somatic cell count, which generally lowers the milk quality. It is estimated that mastitis may cost the dairy industry billions of dollars per year in economic losses.

A growing concern in the treatment of *S. aureus* is that the bacterium is often resistant to multiple antibiotics. Roughly half of the nosocomial isolates in the United States are methicillin-resistant *S. aureus* (MRSA). Methicillin-resistant *S. aureus* is also sometimes referred to as "multidrug-resistant" *S. aureus* or "oxacillin-resistant *S. aureus*." MRSA bacterium is generally resistant to beta-lactam antibiotics, which include the penicillins (e.g., methicillin, dicloxacillin, nafcillin, oxacillin, etc.) and cephalosporins. Currently, a vaccine that prevents staphylococcal disease is unavailable.

A possible approach for staphylococcal vaccine development is to target virulence factors such as toxins, enzymes, polysaccharide capsules, adhesive factors, and the like. A key to the possible vaccine approach may be that the anterior nares of humans are known to be an important niche for *S. aureus*. It is believed that nasal carriage is a major risk factor for invasive infection.

One potential *S. aureus* virulence factor is the iron-regulated surface determinant A (IsdA). IsdA is an *S. aureus* surface adhesin protein that may be immunogenic in certain organisms. IsdA can bind to human desquamated nasal epithelial cells and is believed to play a critical role in nasal colonization.

However, a major obstacle in vaccine development of *S. aureus* is the lack of immunostimulatory adjuvants that can function from mucosal surfaces. While certain toxins (e.g., cholera toxin and heat-labile toxin) have the ability to induce mucosal and systemic immune responses to co-administered antigens, these bacterial proteins are generally too toxic for human use.

SUMMARY OF THE INVENTION

The present invention relates to infectious diseases and, more particularly, to chimeric protein vaccines and methods of use thereof in the treatment of *Staphylococcus aureus*.

In some embodiments, the present invention provides methods of generating an immune response in a mammal comprising: administering to the mammal a composition comprising: a chimeric protein comprising at least one of: a portion of a cholera toxin, a portion of a heat-labile toxin, and a portion of a shiga toxin; and an antigen comprising at least one of: an antigenic material from *S. aureus* and an antigenic material from an *S. aureus*-specific polypeptide.

In other embodiments, the present invention provides a method of inducing an immune response in a cow comprising: administering to the cow a chimeric protein comprising: an adjuvant selected from the group consisting of: a portion of a cholera toxin, a portion of a heat-labile toxin, a portion of a shiga toxin, and any combination thereof; and an antigen selected from the group consisting of: an antigenic material from *S. aureus*, an antigenic material from a *S. aureus*-specific polypeptide, and any combination thereof.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

FIGS. 1A-1C show ribbon diagrams illustrating structures of cholera toxin, IsdA, and chimeric protein according to some embodiments.

FIG. 2 shows a diagram illustrating a plasmid that encodes a chimeric protein according to some embodiments.

FIGS. 3A-3B illustrate expression and purification of a chimeric protein according to some embodiments.

FIG. 4 shows a plot showing the results of a receptor binding affinity assay according to some embodiments.

FIGS. 5A-5D show confocal images of chimeric protein binding to Vero and DC2.4 cells stained with fluorescent dyes according to some embodiments.

FIG. 6 shows a plot showing in vivo systemic antibody response to chimeric protein according to some embodiments.

Figure 7:
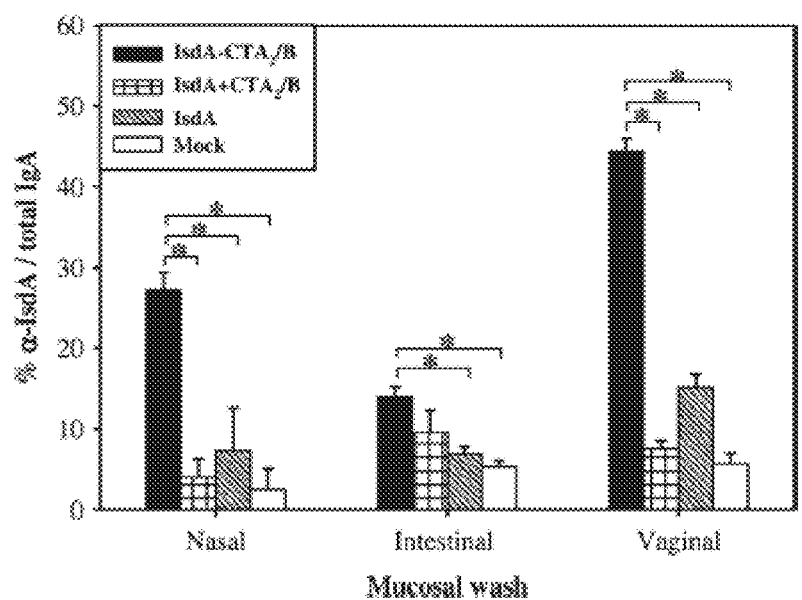
FIG. 7 shows a plot illustrating in vivo mucosal antibody response to chimeric protein according to some embodiments.
Figures 8A, 8C:
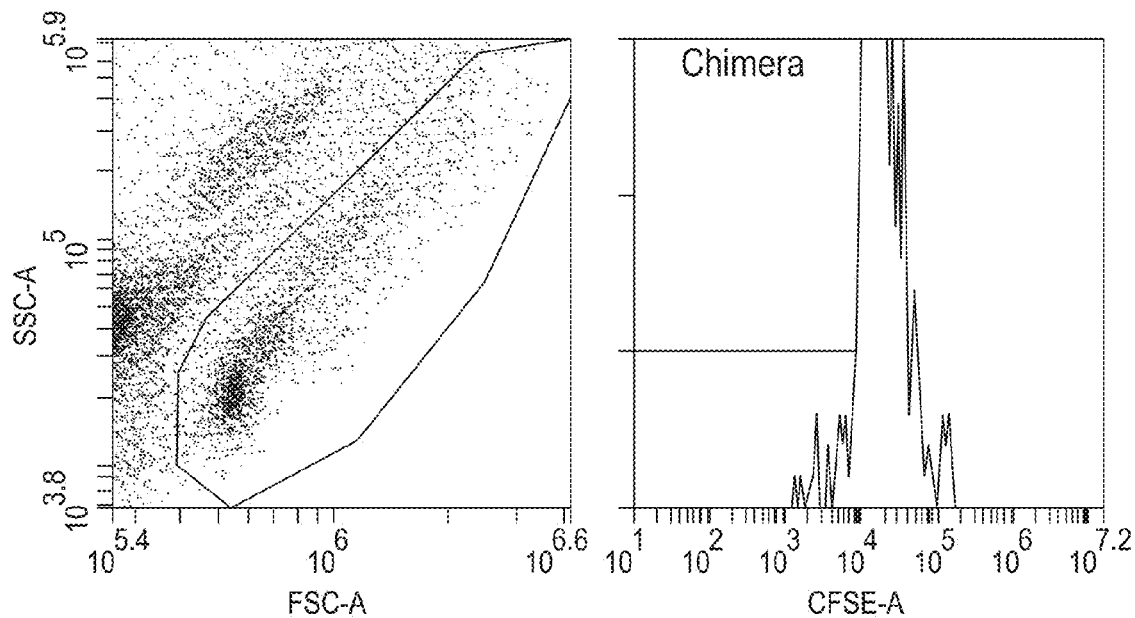
FIGS. 8A-8D show plots showing the results of flow cytometry experiments on the proliferation of T lymphocytes from mice immunized with chimeric protein according to some embodiments.
Figures 8B, 8D:
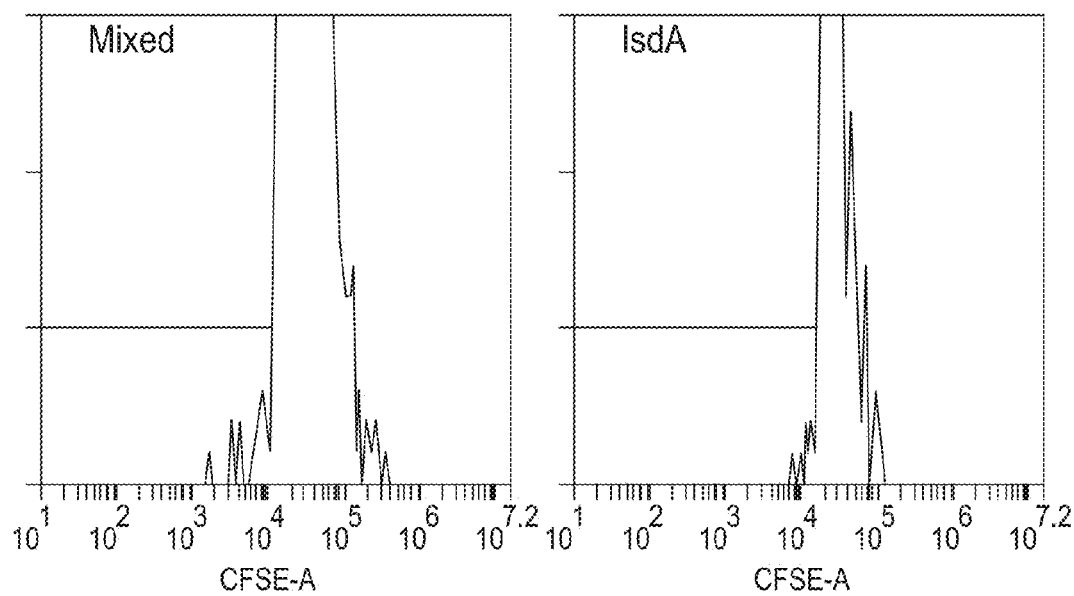

DETAILED DESC previously difficult to separate the toxigenicity and adjuvanticity of cholera toxin, heat-labile toxin, and/or shiga toxin.

In some embodiments, the adjuvant source may be a toxin. The adjuvant may be coupled, assembled, folded, fused, or otherwise associated with an antigen to form a composition that further enhances the immunogenic effects of the antigen. Examples of suitable toxins include, but are not limited to, cholera toxin (CT), shiga toxin (ST1, ST2, etc.), heat-labile toxin (LT, LT-IIa, LT-IIb, etc.) from *E. coli*. In some preferred embodiments, the toxins are modified to be non-toxigenic while remaining potent immunostimulatory molecules that can bind to and target immune effector cells at mucosal site. It is believed that both shiga toxin and heat-labile toxin are structurally similar or analogous to cholera toxin.

In particular, cholera toxin is a protein secreted by the bacterium *Vibrio cholerae* and is generally responsible for the massive, watery diarrhea characteristic of cholera infection. Structurally, cholera toxin is an oligomeric complex made up of six protein subunits: a single copy of the A subunit (part A, enzymatic), and five copies of the B subunit (part B, receptor binding). The A subunit has two important segments: the A1 domain (CTA$_1$), which is toxigenic and the A2 domain (CTA$_2$), which forms an extended alpha helix that sits snugly in the central pore of the B subunit ring.

FIG. 1A shows a ribbon diagram of the cholera toxin crystal structure showing the CTA$_1$ domain (SEQ ID NO: 1) and connecting CTA$_2$ domain (SEQ ID NO:2), and the B subunit (SEQ ID NO: 3).

It is believed that cholera toxin immunomodulation may be involved in the activation of antigen-presenting cells, promotion of B-cell isotype switching, and upregulation of costimulatory and major histocompatibility complex (MHC) class II expression. Many of these responses result from the interaction of the cholera toxin B (CTB) subunit with the ganglioside GM1 receptor on effector cells, such as dendritic cells, that promote antigen uptake, presentation, and cellular activation. Thus, suitably modified non-toxigenic forms of cholera toxin by themselves may act as an antigen carrier and be highly immunostimulatory. Without being limited by theory, it is believed that heat-labile toxin and shiga toxin are structurally and functionally similar (e.g., adjuvanticity) to the cholera toxin. For example, heat-labile toxin has an A$_1$ domain (SEQ ID NO: 7), A$_2$ domain (SEQ ID NO: 8), B domain (SEQ ID NO: 9) analogous to the A$_1$, A$_2$, and B domains of cholera toxin. An IsdA-LTA$_2$/B chimeric protein may have a sequence shown in SEQ ID NO: 10.

An antigen is generally any substance that causes the production of antibodies against it. An antigen may be a foreign substance from the environment or it may also be formed within the environment, such as bacterial toxins or tissue cells. Examples of a suitable antigen source include, but are not limited to, iron-regulated surface determinant A (IsdA), iron-regulated surface determinant B (IsdB), clumping factor A (ClfA), clumping factor B (ClfB), fibronectin-binding protein (FnBP), penicillin binding protein 2a (PBP2A), serine-aspartate rich fibrinogen sialoprotein binding protein (SdrE), and the like.

In particular, the N-terminal near iron transporter (NEAT) domain of IsdA is capable of binding to a broad spectrum of human ligands, including transferring heme, fibrinogen, fibronectin, and corneocyte envelope proteins to mediate adherence and dissemination of *S. aureus*. The C-terminal domain of IsdA defends *S. aureus* against human skin bactericidal fatty acids and antimicrobial peptides by making the cell surface hydrophilic.

FIG. 1B shows a ribbon diagram of IsdA antigen (SEQ ID NO: 4) that is replacing the toxigenic CTA$_1$ domain (SEQ ID NO: 1) to construct a chimeric protein that comprises an antigen and a non-toxigenic adjuvant. FIG. 1C shows a ribbon diagram of one preferred chimeric protein, IsdA-CTA$_2$/B (SEQ ID NO: 5).

Some embodiments provide compositions comprising: a chimeric protein comprising at least one of: a portion of a cholera toxin, a portion of a heat-labile toxin, and a portion of a shiga toxin; and an antigen comprising at least one of: an antigenic material from *S. aureus* and an antigenic material from a *S. aureus*-specific polypeptide.

In some embodiments, the composition is a fusion protein. In certain embodiments, the composition is a single polypeptide.

Some embodiments provide a chimeric protein comprising: an adjuvant and an antigen. The adjuvant may be selected from the group consisting of: a portion of a cholera toxin, a portion of a heat-labile toxin, a portion of a shiga toxin, and combinations thereof. The antigen may be selected from the group consisting of: an antigenic material from *S. aureus* (e.g., carbohydrates, peptides, etc.), an antigenic material from an *S. aureus*-specific polypeptide, and combinations thereof.

In some embodiments, the adjuvant is one of: CTA$_2$/B, LTA$_2$/B, or STA$_2$/B. In one or more embodiments, the adjuvant further includes at least one additional cholera toxin B subunit, heat-labile toxin B subunit (e.g., I or II), or shiga toxin B subunit (e.g., I or II). In one or more embodiments, the adjuvant further comprises at least one additional cholera toxin A$_2$ subunit, heat-labile toxin A$_2$ subunit (e.g., I or II), or shiga toxin A$_2$ subunit (e.g., I or II).

While some preferred embodiments of the domain and chimeric protein sequences have been provided, the present invention may be practiced using any number of alternative embodiments. For example, it is well known in the relevant arts that protein or polypeptide variants typically retain their function as long as they have sufficient sequence identity with their native sequences.

In some embodiments, the composition has at least about 80% sequence identity to SEQ ID NO: 5, 10, or 15. In some preferred embodiments, the composition has at least about 90% sequence identity to SEQ ID NO: 5, 10, or 15. In some preferred embodiments, the composition has at least about 95% sequence identity to SEQ ID NO: 5, 10, or 15. In certain embodiments, the antigen portion of the composition has at least about 80% sequence identity to SEQ ID NO: 4. In some preferred embodiments, the antigen portion of the composition has at least about 90% sequence identity to SEQ ID NO: 4. In some preferred embodiments, the antigen portion of the composition has at least about 95% sequence identity to SEQ ID NO: 4. In some embodiments, the composition is assembled from a first polypeptide and a second polypeptide that are non-covalently linked. In one or more of these embodiments, the first polypeptide has at least about 80% sequence identity to SEQ ID NO: 6, 11, or 16. In some preferred embodiments, the first polypeptide has at least about 90% sequence identity to SEQ ID NO: 6, 11, or 16. In some preferred embodiments, the first polypeptide has at least about 95% sequence identity to SEQ ID NO: 6, 11, or 16. In some embodiments, the second polypeptide has at least about 80% sequence identity to SEQ ID NO: 3, 9, or 14. In some preferred embodiments, the second polypeptide has at least about 90% sequence identity to SEQ ID NO: 3, 9, or 14. In some preferred embodiments, the second polypeptide has at least about 95% sequence identity to SEQ ID NO: 3, 9, or 14.

Generally, a chimeric protein will be comprised of a single A$_2$ subunit and a B subunit (from cholera toxin, heat-labile toxin, or shiga toxin). In some optional embodiments, the chimeric protein may further comprise at least one additional B subunit. In some optional embodiments, the B subunit may comprise five identical peptides. In some optional embodiments, the chimeric protein may further comprise at least one additional $A_2$ subunit. In some embodiments, the subunits may be linked by a disulfide bond. In some embodiments, the disulfide bond may be engineered. In some embodiments, the antigen has a disulfide bond with the adjuvant. In some embodiments, the antigen is associated non-covalently with the adjuvant.

In some embodiments, the antigen comprises a sequence that has at least about 80% sequence identity to iron-regulated surface determinant A (IsdA), iron-regulated surface determinant B (IsdB), clumping factor A (ClfA), clumping factor B (ClfB), fibronectin-binding protein (FnBP), fibronectin-binding protein (FnBP), penicillin binding protein 2a (PBP2A), or serine-aspartate rich fibrinogen sialoprotein binding protein (SdrE). In some preferred embodiments, the sequence identity is at least about 90%, or at least about 95%.

In some exemplary embodiments, the chimeric protein is IsdA-$CTA_2$/B (SEQ ID NO: 5). As used herein, "IsdA-$CTA_2$/B" generally refers to a chimeric protein that comprises an IsdA antigen domain, a $CTA_2$ subunit, and a CTB subunit. In some embodiments, each of the IsdA antigen domain (SEQ ID NO: 4), the $CTA_2$ domain (SEQ ID NO: 2) and the CTB domain (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-$LTA_2$/B (SEQ ID NO: 10). As used herein, "IsdA-$LTA_2$/B" generally refers to a chimeric protein that comprises an IsdA antigen domain, a $LTA_2$ subunit, and a LTB subunit. In some embodiments, each of the IsdA antigen domain (SEQ ID NO: 4), the $LTA_2$ subunit (SEQ ID NO: 8) and the CTB subunit (SEQ ID NO: 9) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-$STA_2$/B (SEQ ID NO: 15). As used herein, "IsdA-$STA_2$/B" generally refers to a chimeric protein that comprises an IsdA antigen domain, a $STA_2$ subunit, and a STB subunit. In some embodiments, each of the IsdA antigen domain (SEQ ID NO: 4), the $STA_2$ subunit (SEQ ID NO: 13) and the STB subunit (SEQ ID NO: 14) may be bonded covalently (e.g., peptide bonds, disulfide bonds, etc.) or non-covalently to at least one other domain. In some embodiments, the bond may be an engineered disulfide bond.

In some embodiments, the chimeric protein is IsdB-$CTA_2$/B (amino acids 24-367 of SEQ ID NO: 22). As used herein, "IsdB-$CTA_2$/B" generally refers to a chimeric protein that comprises an IsdB antigen domain, a $CTA_2$ subunit, and a CTB subunit. In some embodiments, each of the IsdB antigen domain (amino acids 42-338 of SEQ ID NO: 23), the $CTA_2$ subunit (SEQ ID NO: 2) and the CTB subunit (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein is ClfA-$CTA_2$/B (amino acids 24-347 of SEQ ID NO: 24). As used herein, "ClfA-$CTA_2$/B" generally refers to a chimeric protein that comprises a ClfA antigen domain, a $CTA_2$ subunit, and a CTB subunit. In some embodiments, each of the ClfA antigen domain (amino acids 287-559 of SEQ ID NO: 25), the $CTA_2$ subunit (SEQ ID NO: 2) and the CTB subunit (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein may further comprise modifications that enhance at least one of: solubility of the chimeric protein, specificity for S. aureus, specificity for GM1, expression of the chimeric protein, and immunogenicity of the chimeric protein.

Some embodiments provide methods for generating an immune response in a mammal comprising: administering to the mammal a composition (e.g., chimeric protein) according to one or more embodiments described herein.

In some embodiments, the mammal is selected from the group consisting of: a human, a cow, a dog, a cat, and a horse.

In some embodiments, the administration of the composition is by intranasal administration, oral administration, intramuscular administration, peritoneal administration, sublingual administration, transcutaneous administration, subcutaneous administration, intravaginal administration, intramammary administration or intrarectal administration. The administered dosage of the composition may generally be an amount suitable to elicit the desired immune response. In some embodiments, the administering to the mammal comprises: administering the composition to at least one cell from the mammal in vitro or in vivo.

Some embodiments provide methods for inducing an immune response in a cow comprising: administering to the cow, a chimeric protein according to one or more embodiments described herein.

To facilitate a better understanding of the present invention, the following examples of preferred embodiments are given. In no way should the following examples be read to limit, or to define, the scope of the invention.

EXAMPLE 1

To direct the IsdA-$CTA_2$ and CTB peptides of the chimera to the E. coli periplasm for proper assembly, pBA001 (FIG. 2) was constructed from pARLDR19, which utilizes the E. coli LTIIb N-terminal leader sequence. Induction of pBA001 and purification from the periplasm of E. coli resulted in efficient IsdA-$CTA_2$/B production (3 to 4 mg from 1 liter of starting culture). SDS-PAGE analysis of the purification of IsdA-$CTA_2$/B and immunoblotting using antibodies against CTA and CTB (FIG. 3A) confirm that IsdA-$CTA_2$ (~38 kDa) was copurified with CTB (~11 kDa) on D-galactose agarose, which is indicative of proper chimera folding. Referring to FIG. 3A, the SDS-PAGE analysis shows flowthrough (FT), washes (W1 and W2) and elution (E) of IsdA-$CTA_2$/B from D-galactose affinity purification and anti-CTA/B Western blot of purified IsdA-$CTA_2$/B (~38 and 11 kDA).

IsdA alone was also purified using a six-histidine tag (SEQ ID NO: 26). FIG. 3B shows an SDS-polyacrylamide gel of all resulting proteins used in animal studies, as well as immunoblotting of purified IsdA with anti-His6 ("His6" disclosed as SEQ ID NO: 26) (~37 kDa): IsdA-$CTA_2$/B (G1), IsdA plus $CTA_2$/B mixed (G2), and IsdA (G3).

The following protocol was followed in order to obtain the chimeric proteins.

MRSA252 strain was used for IsdA isolation. MRSA USA300 (pvl mutant) strain was used in adhesion assays. E. coli TE1, a ΔendA derivative of TX1, and BL21(DE3)/pLysS strains were used for protein expression. All bacterial strains were cultured using Luria-Bertani (LB) agar or broth at 37° C. with chloramphenicol (35 μg/ml), ampicillin (100 μg/ml), and/or kanamycin (50 μg/ml).

To construct pBA001 plasmid (FIG. 2) for the expression of IsdA-CTA$_2$/B, IsdA was PCR amplified from MRSA252 with primers that add 5' SphI GCTACTGGCATGCGGCAA-CAGAAGCTACGAAC (SEQ ID NO: 17) and 3' ClaI GTG-CATGATCGATTTTGGTAATTCTTTAGC (SEQ ID NO: 18) sites (in boldface) and cloned into pARLDR19 between the LTIIb leader sequence and CTXA$_2$. CTB was also expressed from this vector. To make His6-IsdA IsdA ("His6" disclosed as SEQ ID NO: 26), IsdA was amplified from MRSA252 with primers that add 5' BamHI GCTACTG-GATCCGCGGCAACAGAAGCTACGAAC (SEQ ID NO: 19) or GTGCATAAGCTTTCAAGTTTTTGGTAAT-TCTTTAGC (SEQ ID NO: 20) and 3' HindIII GTGCAT-GATCGATTTTGGTAATTCTTTAGC (SEQ ID NO: 21) sites (in boldface) and cloned into pTrcHisA (Invitrogen, Carlsbad, Calif.) or pET-40b+, yielding pBA009A and pBA015. pARLDR19 was used to express CTA$_2$/B for the mixed preparation. Plasmids were transformed into *E. coli* TE1 (pBA001, pBA009A, and pARLDR19) or BL21(DE3)/pLysS (pBA015) and sequenced.

To express IsdA-CTA$_2$/B and CTA$_2$/B, cultures with pBA001 or pARLDR19 were grown to an optical density at 600 nm (OD$_{600}$) of 0.9 and induced for 15 h with 0.2% L-arabinose. Proteins were purified from the periplasmic extract using immobilized D-galactose. For mock cultures, *E. coli* TE1 without plasmid was induced, and the periplasmic extract was purified. IsdA was isolated from the cytosol of cultures containing pBA009A and purified by cobalt affinity chromatography under denaturing conditions. IsdA was also purified from periplasmic extracts of cultures containing pBA015 over Talon resin under native conditions. All proteins were dialyzed against phosphate-buffered saline (PBS), reduced to <0.125 endotoxin units (EU)/ml lipopolysaccharide by passage through an endotoxin removal column, and quantified by bicinchoninic acid assay prior to the addition of 5% glycerol.

Proteins resolved by SDS-12% PAGE were stained with COOMASSIE™ or transferred to nitrocellulose membranes. Membranes were blocked overnight with 5% skim milk in PBS plus 0.05% TWEEN 20™ (PBS-T), incubated with polyclonal anti-CTA (1:2,500) and anti-CTB (1:5,000) or anti-His6 ("His6" disclosed as SEQ ID NO: 26) (1:2,500), followed by horseradish peroxidase (HRP)-conjugated anti-rabbit IgG (1:5,000) and developed with IMMOBILON WESTERN HRP St. BS commercially available from Millipore, Billerica, Mass.

EXAMPLE 2

To compare the receptor binding affinity of purified IsdA-CTA$_2$/B chimera with native CT, ganglioside GM1 ELISA assays using anti-CTA and anti-CTB antibodies were performed.

GM1 enzyme-linked immunosorbent assays (ELISA) were performed by coating microtiter plates with 0.15 µM GM1 for 15 h at 20° C., blocking with 10% bovine serum albumin, and incubating with IsdA-CTA$_2$/B or CT for 1 h at 37° C. Ganglioside GM1 is found ubiquitously on mammalian cells and acts as the site of binding for both cholera toxin and heat-labile toxin. Plates were washed with PBS-T and incubated with anti-CTA (1:2,000) or anti-CTB (1:5,000) followed by HRP-conjugated anti-rabbit IgG, both for 1 h at 37° C. The reaction was developed with o-phenylenediamine dihydrochloride (A$_{450}$).

The ELISA results indicate that the B subunit of IsdA-CTA$_2$/B has GM1 binding affinity similar to that of CT (FIG. 4). Low anti-CTA response from IsdA-CTA$_2$/B was an expected result from this fusion that contains only 46 bp of full-length CTA.

Confocal microscopy was used to further confirm receptor binding and internalization of IsdA-CTA$_2$/B into epithelial and dendritic cells (DC) in vitro. Immune effector cells, such as dendritic cells, have a uniquely high affinity for CT and non-toxigenic CTB. FIGS. 5A-5D show anti-CT FITC-labeled IsdA-CTA$_2$/B bound to the surface of cells (Vero epithelial cells in FIG. 5A-5B; DC cells in FIG. 5C-5D) at 4° C. and internalization after 45 min at 37° C., indicating that, at a minimum, the CTB subunit of the chimera were efficiently imported into the cell. These images obtained using polyclonal anti-CT and anti-rabbit-FITC with DAPI suggest that IsdA-CTA$_2$/B was binding and transporting into Vero and DC2.4 cells. Cells were incubated with IsdA-CTA$_2$/B for 45 minutes at 4° C. to inhibit, or at 37° C. to promote cellular uptake.

EXAMPLE 3

The chimeric proteins were tested for their specific humoral response.

BALB/c mice were mock immunized or immunized intranasally with IsdA-CTA$_2$/B, IsdA plus CTA$_2$/B mixed, or IsdA on day 0 and boosted on day 10 (Table 1 below). FIG. 6 shows systemic antibody response to IsdA-CTA$_2$/B in vivo. Referring to FIG. 6, sera collected on days 0, 10, 14, and 45 were pooled by treatment group at each time point and tested for recognition of IsdA by IgG ELISA. IsdA-specific serum IgG endpoint titers from mice immunized with IsdA-CTA$_2$/B were significantly higher than those of mock-immunized mice on day 10, than those of all control groups on day 14, and than those of mice immunized with IsdA alone and mock-immunized mice on day 45. As used herein, "*" denotes statistical significance (P<0.05) between mice immunized with IsdA-CTA$_2$/B versus controls. Nasal, intestinal, and vaginal washes were collected on day 45, pooled by treatment group, and tested for recognition of IsdA by IgA ELISA.

FIG. 7 shows mucosal antibody response to IsdA-CTA$_2$/B in vivo. Referring to FIG. 7, the percentage of IsdA-IgA out of total IgA was significantly higher in nasal and vaginal washes from mice immunized with IsdA-CTA$_2$/B than from mock-immunized mice, mice immunized with IsdA plus CTA$_2$/B, or mice immunized with IsdA alone. In addition, intestinal IsdA-IgA was significantly higher in IsdA-CTA$_2$/B-immunized mice than in IsdA- and mock-immunized mice (FIG. 7). Together, these results suggest that IsdA specific systemic and mucosal humoral immunity can be stimulated after intranasal vaccination with the IsdA-CTA$_2$/B chimera.

TABLE 1

| Immunization Strategy. | | | | |
|---|---|---|---|---|
| | Dose per | | | Days of sampling |
| Antigen/ adjuvant | vaccination (µg) | n[b] | Days of intranasal vaccination | Sera | Mucosal secretions and spleen (n) |
| IsdA – CTA$_2$/B chimera | 50 | 8 | 0, 10 | 0, 10, 14, 45 | 14 (2), 45 (6) |
| IsdA + CTA$_2$/B | 17 + 33[a] | 8 | 0, 10 | 0, 10, 14, 45 | 14 (2), 45 (6) |

TABLE 1-continued

Immunization Strategy.

| Antigen/ adjuvant | Dose per vacci- nation (µg) | n[b] | Days of intranasal vaccination | Days of sampling | |
|---|---|---|---|---|---|
| | | | | Sera | Mucosal secretions and spleen (n) |
| IsdA | 17 | 8 | 0, 10 | 0, 10, 14, 45 | 14 (2), 45 (6) |
| Mock | NA[c] | 8 | 0, 10 | 0, 10, 14, 45 | 14 (2), 45 (6) |

[a]Concentrations are according to equimolar to equimolar amounts of IsdA
[b]n, number of mice
[c]NA, not applicable

EXAMPLE 4

Figure 9:
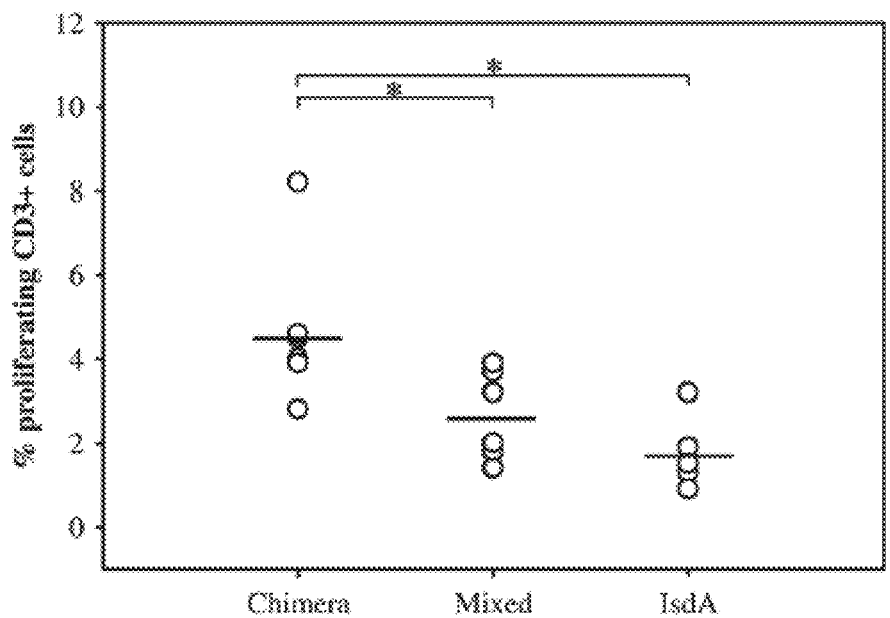
FIG. 9 shows a plot summarizing the flow cytometry results shown in FIGS. 8A-8D according to some embodiments.

Cellular proliferation of IsdA-stimulated splenocytes was assessed using flow cytometry and a resazurin-based fluorescent dye assay. CFSE-based flow cytometric results suggest that day 45 splenocytes derived from mice immunized with IsdA-CTA$_2$/B showed significant proliferation of IsdA-specific CD3+ T lymphocytes compared with mixed and IsdA control groups (FIGS. 8A-8D and 9). Referring to FIGS. 8A-8D, CFSE-labeled splenocytes were cultured in vitro for 84 h with IsdA and stained with anti-CD3-PE-Cy5. Referring to FIG. 9, percent proliferation of IsdA-specific CD3+ T lymphocytes from individual mice on day 45 was determined by flow cytometry. Mock samples contained low numbers of CD3+ T lymphocytes.

Figure 10:
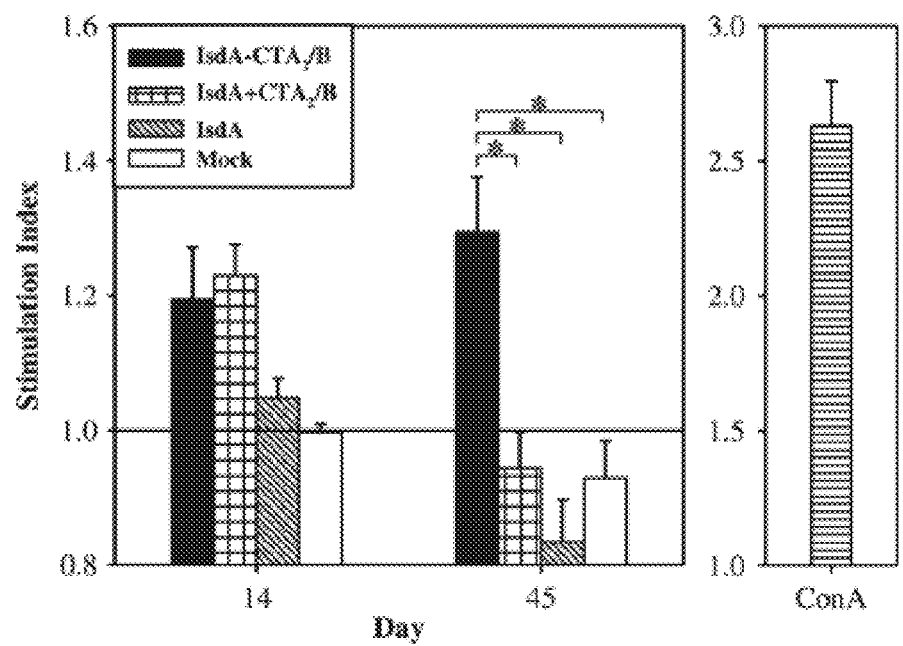
FIG. 10 shows a plot showing the results of Resazurin assay of splenocytes from mice immunized with chimeric protein according to some embodiments.

FIG. 10 shows the result of a resazurin assay of splenocytes from days 14 and 45 cultured in vitro for 84 h with IsdA. The resazurin assays revealed that in vitro stimulation of splenocytes from IsdA-CTA$_2$/B-immunized mice induced significant proliferation compared with IsdA plus CTA$_2$/B, IsdA, and mock groups on day 45 (FIG. 10). With the low sample size (n=2 per group) on day 14, no significance was observed between groups. Error bars are based on n=2 (day 14) or n=6 (day 45). Stimulation was observed for the positive control, ConA. These results suggest that intranasal administration of IsdA-CTA$_2$/B can induce a cellular activation response.

EXAMPLE 5

Figure 11:
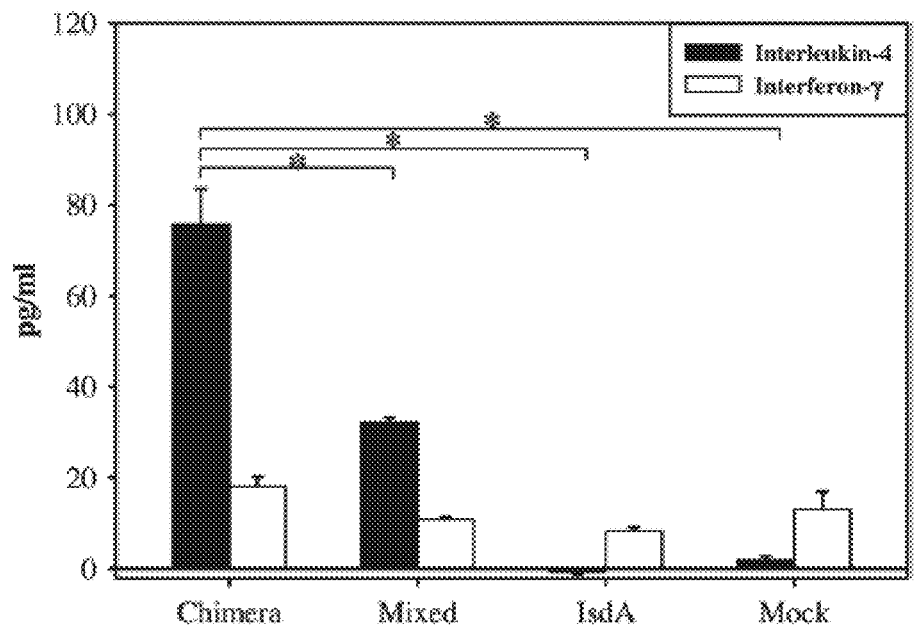
FIG. 11 shows a plot showing IL-4 and IN-γ levels of antigen-stimulated splenocytes from mice immunized with chimeric protein according to some embodiments.

The levels of IL-4 and IFN-γ in supernatants of splenocytes stimulated with IsdA in vitro were determined by ELISA. Referring to FIG. 11, IL-4 and IFN-γ levels in culture supernatants from splenocytes, pooled by immunization group (n=6), were stimulated in vitro for 84 h with IsdA and measured by ELISA. The splenocytes obtained from mice immunized with IsdA-CTA$_2$/B secreted high levels of IL-4, and these levels were significantly higher than levels of all controls (FIG. 11). Although the level of IFN-γ was slightly higher in IsdA-CTA$_2$/B-immune splenocytes, low levels of IFN-γ, near the detection limit for the assay, were found in all groups (FIG. 11).

Figure 12:
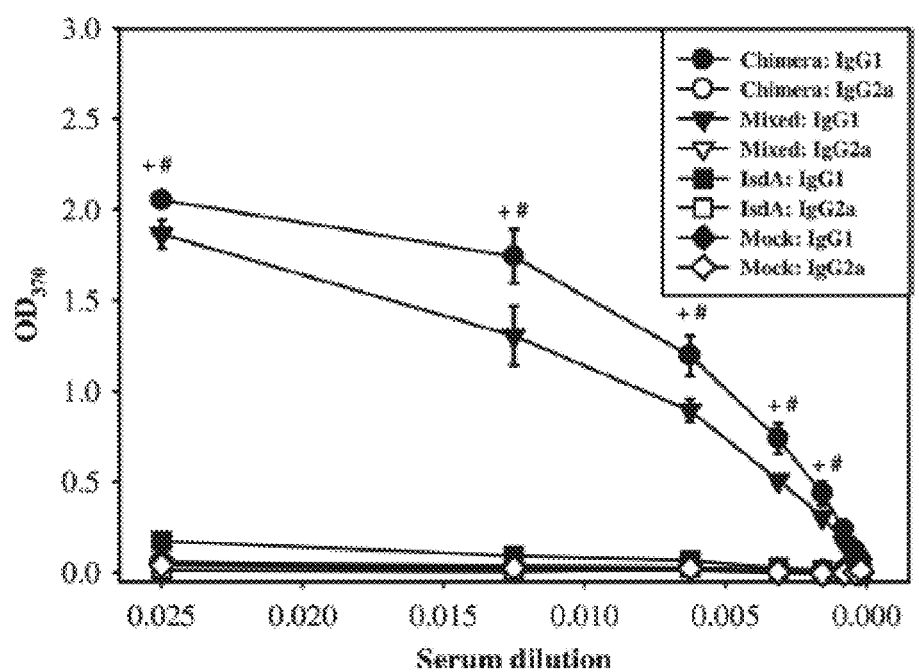
FIG. 12 shows a plot showing the results of IsdA-specific ELISA titrations of systemic antibody subtypes according to some embodiments.

FIG. 12 shows IsdA-specific IgG1 and IgG2a ELISA titrations from day 45 sera pooled by immunization group (n=6). Titrations of IgG1 and IgG2a revealed that immunization with IsdA-CTA$_2$/B drove isotype switching primarily to the IgG1 subclass although minute IgG2a levels were also detected. These results suggest that immunization with IsdA-CTA$_2$/B promotes a Th2-type immune response.

EXAMPLE 6

Figure 13A:
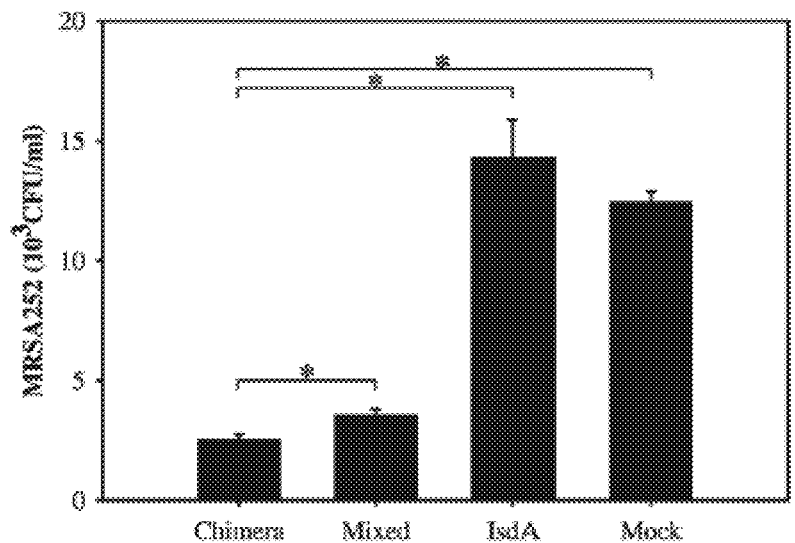
FIGS. 13A-13B show a plot showing the effects of immune serum on S. aureus adhesion to human epithelial cells according to some embodiments.
Figure 13B:
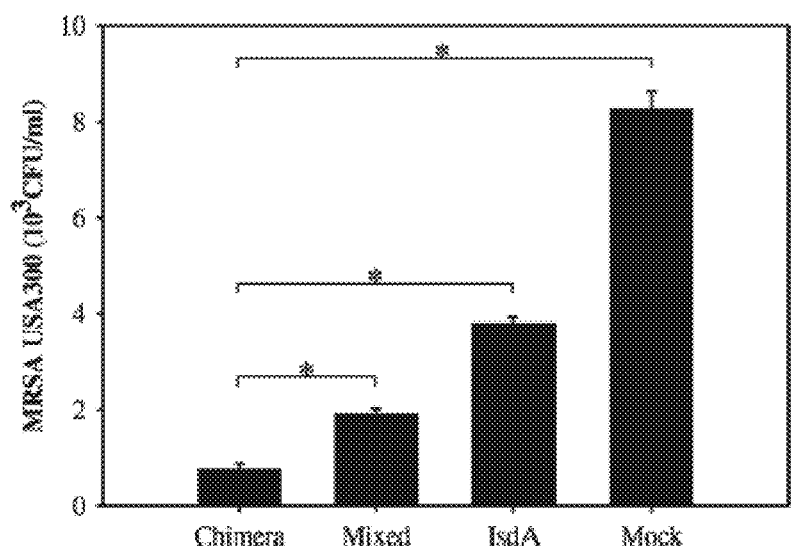
Figure 14:
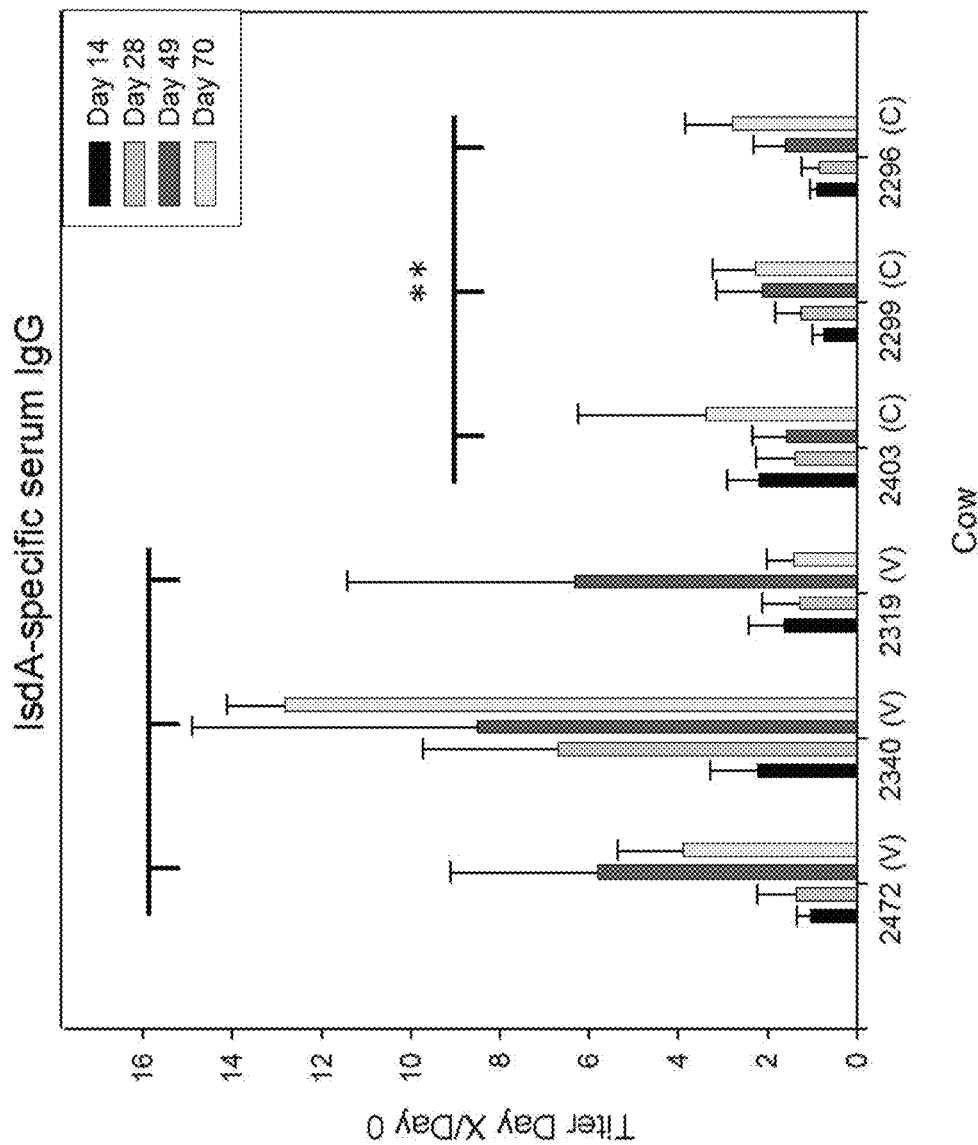
FIG. 14A is a graph showing IsdA specific IgG serum titers in cows treated with IsdA-CTA$_2$/B (V) or control IsdA (C).
FIG. 14B is a graph showing IsdA specific IgG milk titers in cows.
FIG. 14C is a graph showing IsdA-specific IgA milk titers in cows.
FIG. 14D is a graph showing IsdA-specific IgA nasal secretion titers in cows.
FIG. 14E is a graph showing somatic cell counts in cows treated with IsdA-CTA$_2$/B or control IsdA.
Figure 14:
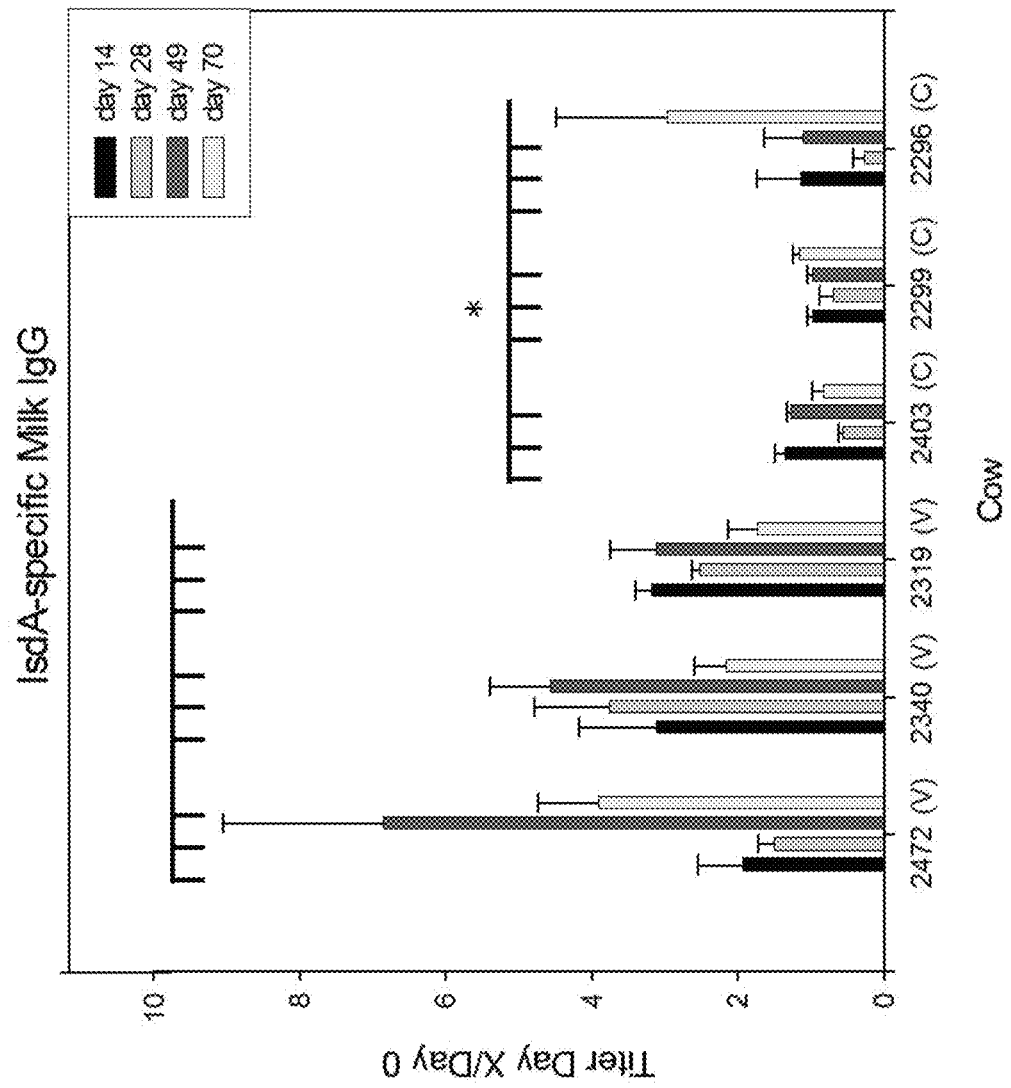
Figure 14:
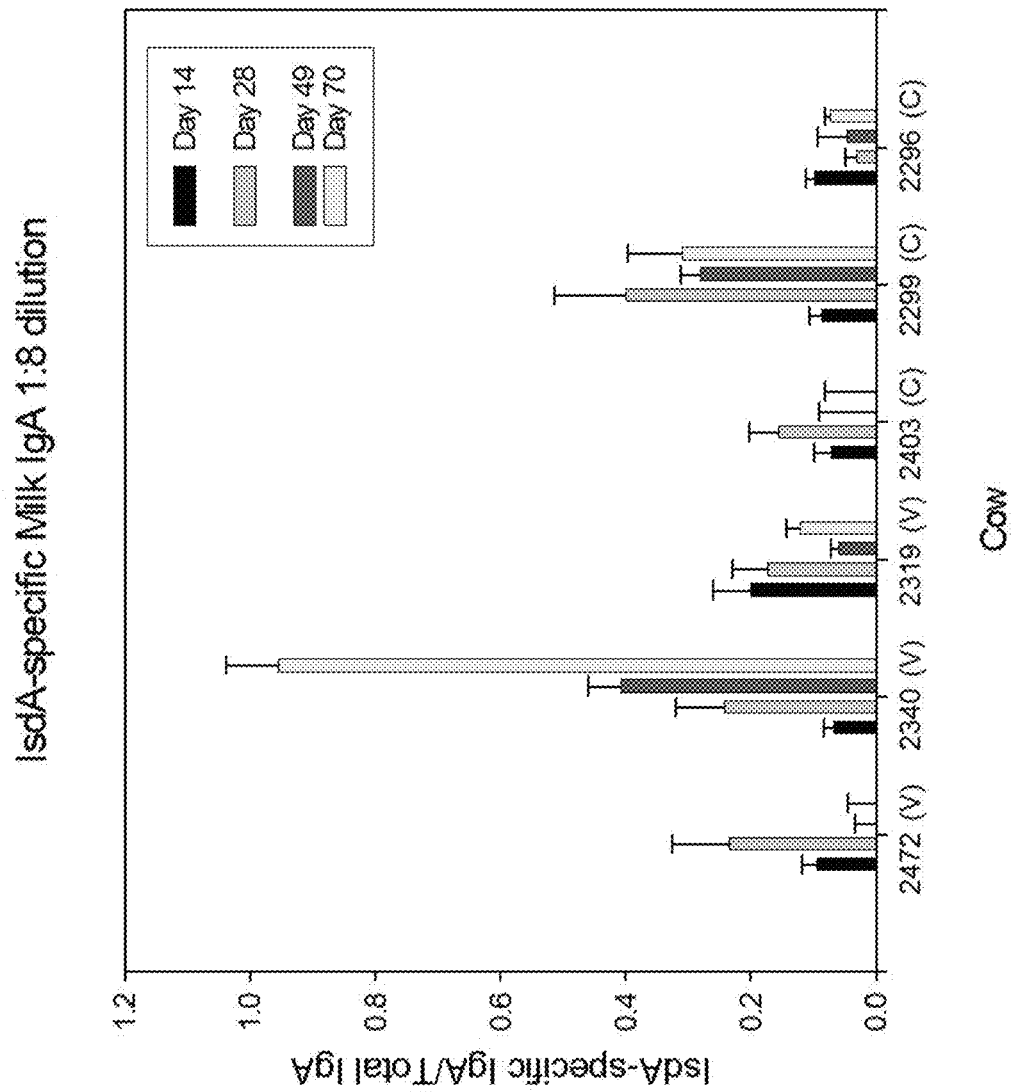
Figure 14:
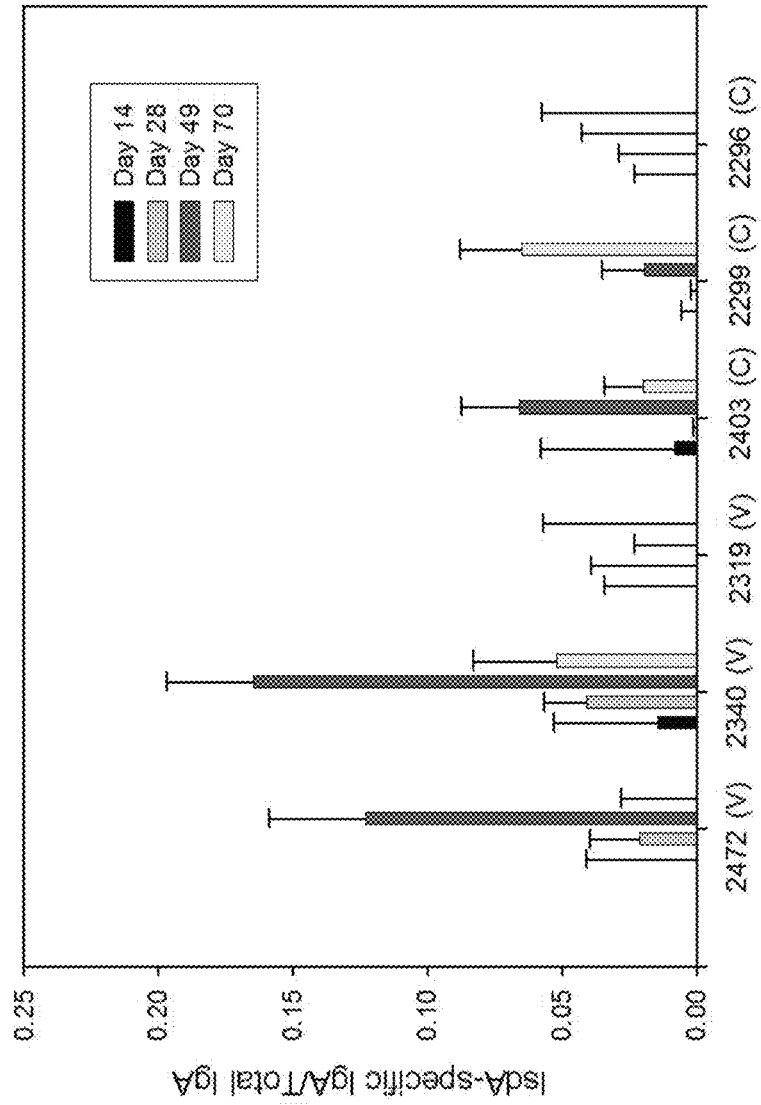
Figure 14:
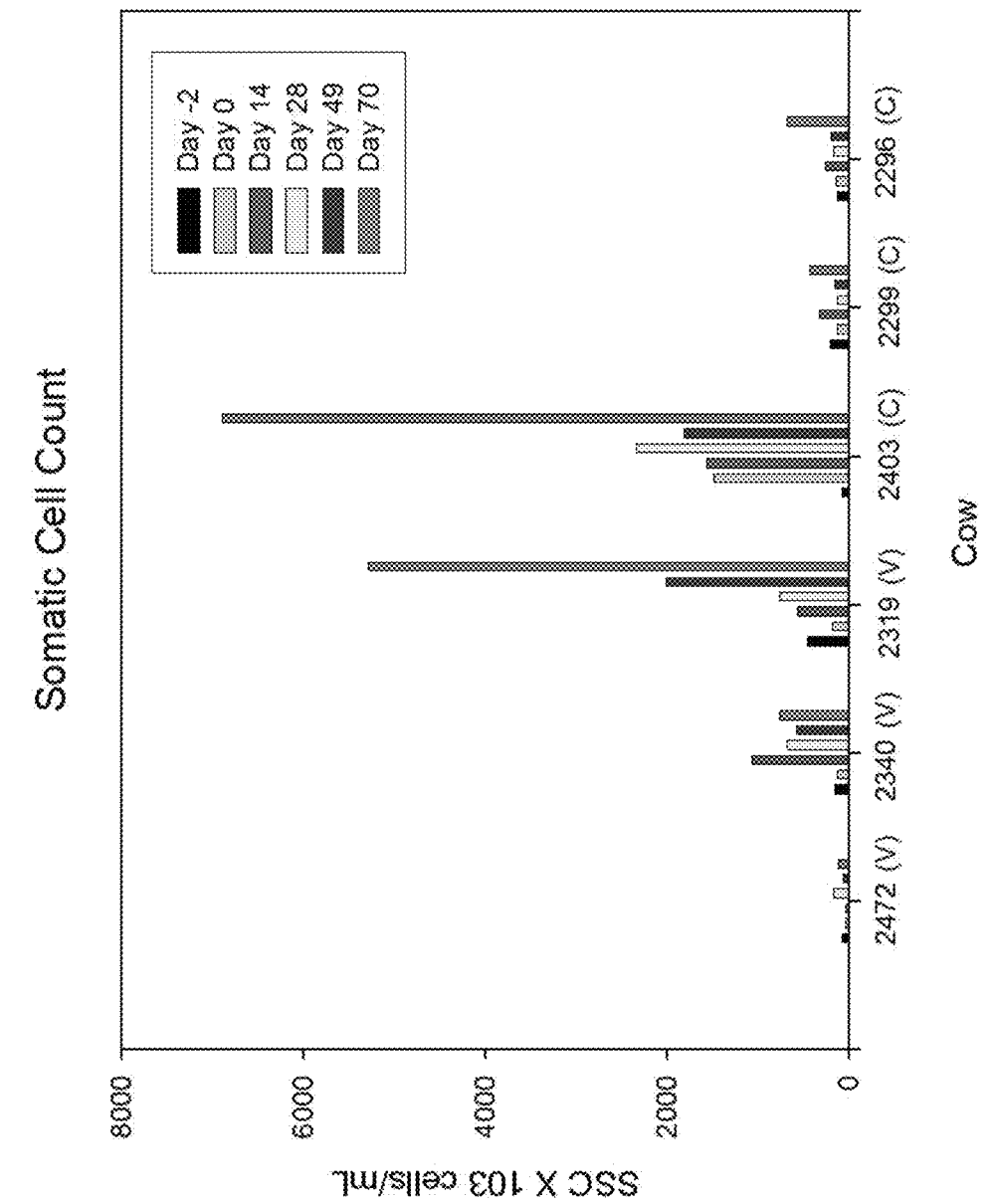

Pooled sera from commonly immunized mice were used to investigate the ability of immune serum to functionally block adherence of *S. aureus* to human epithelial cells (HeLa). FIGS. 13A-13B show the effect of immune serum on *S. aureus* adhesion to human epithelial cells in vitro. Referring to FIG. 13A, sera (1:100; day 45) was pooled by immunization group and incubated with MRSA252 (5×10$^7$ CFU) for 1 h at 37° C. and then added to confluent HeLa cells. After washing and lysis, the number of internalized and cell-bound bacteria was enumerated. Preincubation of the *S. aureus* strain used for vaccination (MRSA252) with day 45 sera from IsdA-CTA$_2$/B-immunized mice significantly reduced bacterial adhesion to epithelial cells compared to all control groups (FIG. 13A).

FIG. 13B shows the result of similar tests performed with MRSA USA300 (5×10$^9$ CFU). Referring to FIG. 13B, there was a significant reduction in bacterial adhesion to human epithelial cells after a different strain of *S. aureus* (MRSA USA300) was preincubated with day 45 sera from mice immunized with IsdA-CTA$_2$/B (FIG. 13B).

These examples suggest that the chimeric proteins of the present invention can bind and transport into epithelial and dendritic cells as consistent with the uptake of CT involving retrograde movement to the perinuclear domain of the Golgi apparatus and endoplastmic reticulum. It is believed that the ability of the chimeric proteins to bind to GM1 and trigger internalization leads to the activation of immune effector cells by the CTB subunit and promotes antigen presentation on MHC molecules.

Moreover, the ELISAs of IsdA-specific responses from the sera and nasal, intestinal, and vaginal fluids of intranasally immunized mice verifies that the chimeric proteins can induce antigen-specific systemic and mucosal immunity in mice. As expected, IgG titers were highest on day 14 after the boost and began to diminish by day 45.

These results also suggest the characteristic ability of CT to induce systemic IgG to antigens co-administered with CT at mucosal sites. The presence of IsdA-specific IgA in nasal, intestinal, and vaginal fluids after intranasal immunization with IsdA-CTA$_2$/B suggests that IgA blasts migrated from the nasal-associated lymphoid tissue into distal mucosal effector sites in the nasal passage and gastrointestinal and genital tracts. Thus, it is believed that CT and CT derivatives promote more of a Th2-type response, which is typically characterized by secretion of IL-4 leading to induction of antibody class switching to non-complement-activating IgG1. In vitro functional assays of antibodies revealed a significant reduction in internalized and cell-bound bacteria on human epithelial cells after preincubation of IsdA-CTA$_2$/B immune serum with the *S. aureus* isolate used for vaccination, MRSA252. Additionally, antibodies were able to prevent adhesion of MRSA USA300.

IsdA from MRSA252 and MRSA USA300 has 92% amino acid identity with the majority of differences present within the C terminus, which suggests that antibodies against IsdA are functional in vitro and may protect against multiple serotypes in vivo.

The results also suggest that the humoral and cellular responses induced by IsdA-CTA$_2$/B are superior to those stimulated by a mixed preparation of antigen and adjuvant (IsdA plus CTA$_2$/B). Thus, the structure of the IsdA-CTA$_2$/B chimera is optimal for the induction of antigen-specific humoral responses and potentially for presentation on MHC molecules.

EXAMPLE 7

To direct the ClfA-CTA$_2$ and CTB peptides of the chimera to the *E. coli* periplasm for proper assembly, pSKJ001 (FIG.

Figure 15:
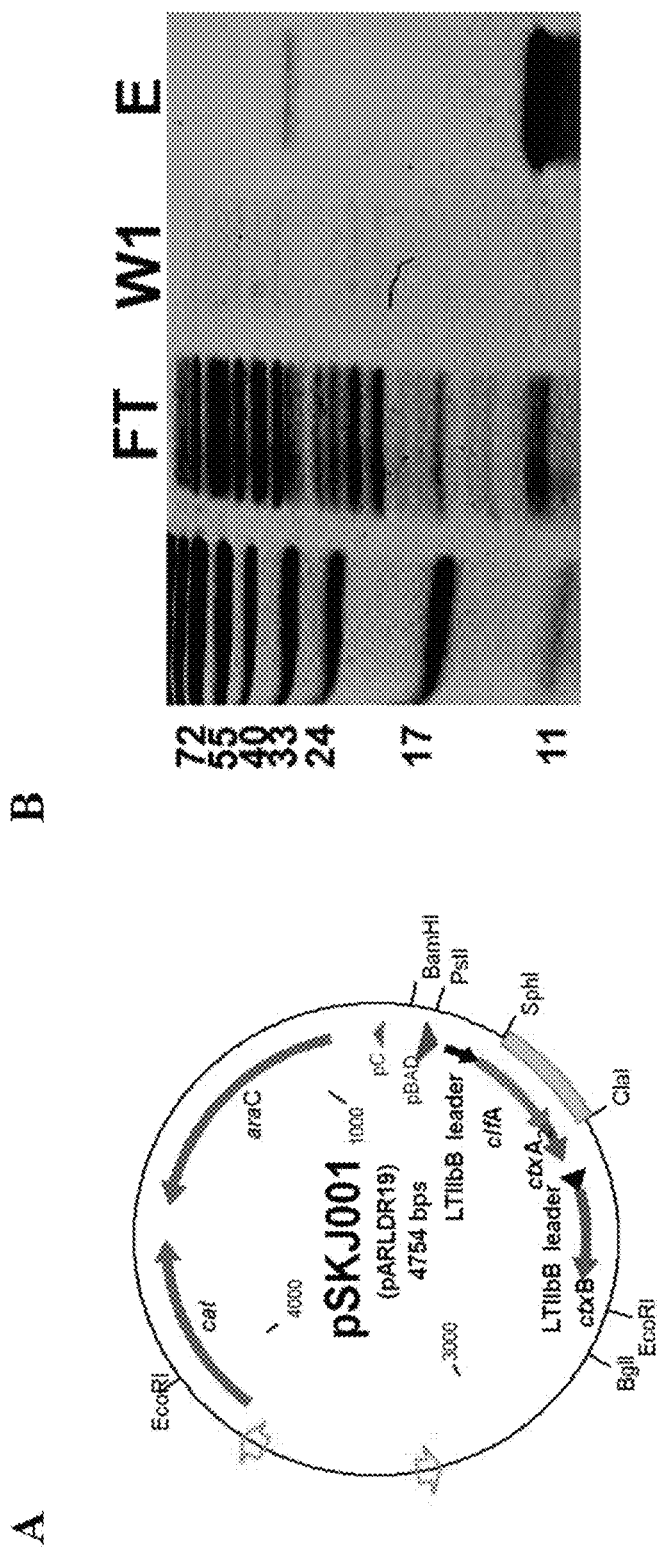
FIG. 15A is an illustration of a plasmid pSKJ001 for expression of ClfA-CTA$_2$/B.
FIG. 15B is an image of SDS-PAGE of the S. aureus ClfACTA$_2$/B chimera (ClfA-CTA$_2$ approximately 37 kD, CTB equals 11.5 kD). FT=flow through, W1=wash 1, E=elution of D-galactose column.

15A) was constructed from pARLDR19, which utilizes the *E. coli* LTIIb N-terminal leader sequence. SDS-PAGE analysis of the purification of ClfA-CTA$_2$/B confirms that ClfA-CTA$_2$ (~37 kDa) was copurified with CTB (11.5 kDa) on D-galactose agarose, which is indicative of proper chimera folding. Referring to FIG. 15B, the SDS-PAGE analysis shows flowthrough (FT), wash 1 (W1) and elution (E) of ClfA-CTA$_2$/B from D-galactose affinity purification.

Figure 16:
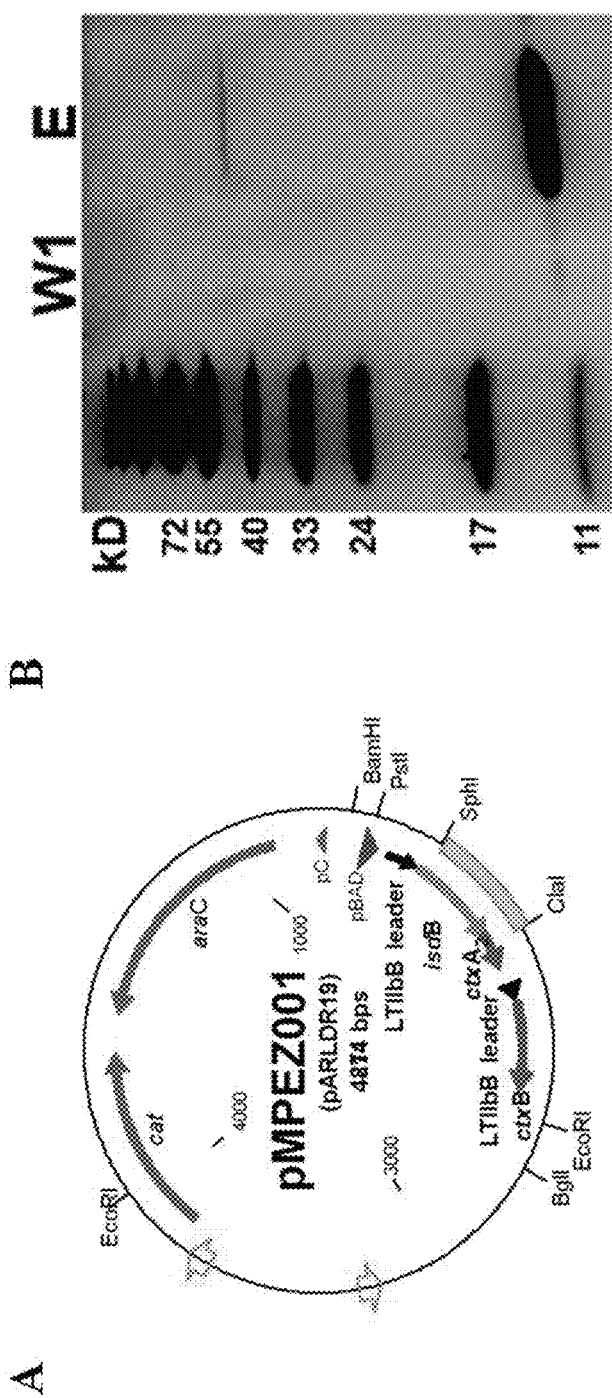
FIG. 16A is an illustration of a plasmid pMPEZ001 for expression of IsdB-CTA$_2$/B.
FIG. 16B is an image of SDS-PAGE of the S. aureus IsdBCTA$_2$/B chimera (IsdB-CTA$_2$ approximately 42 kD, CTB=11.5 kD). W1=wash 1, E=elution of D-galactose column.

To direct the IsdB-CTA$_2$ and CTB peptides of the chimera to the *E. coli* periplasm for proper assembly, pSKJ001 (FIG. 16A) was constructed from pARLDR19, which utilizes the *E. coli* LTIIb N-terminal leader sequence. SDS-PAGE analysis of the purification of IsdB-CTA$_2$/B confirms that IsdB-CTA$_2$ (~42 kDa) was copurified with CTB (11.5 kDa) on D-galactose agarose, which is indicative of proper chimera folding. Referring to FIG. 16B, the SDS-PAGE analysis shows flowthrough (FT), wash 1 (W1) and elution (E) of IsdB-CTA$_2$/B from D-galactose affinity purification.

EXAMPLE 8

Milk anti-IsdA IgA titer levels were measured in cows treated with a chimeric protein according to one or more embodiments of the present invention. Six (2472, 2340, 2319, 2403, 2299, 2296) clinically healthy Holstein dairy cows were vaccinated intranasally on day 0 with 300 μg of IsdA-CTA$_2$/B chimera (cows 2472, 2340, 2319) or an equivalent concentration of IsdA alone (cows 2403, 2299, 2296). Cows were boosted on day 14 with the same concentration. Milk was collected on days 0, 14 and 28 and analyzed by IsdA-specific IgA ELISA. Immunogenicity of the IsdA-CTA$_2$/B chimera was measured after intranasal delivery in dairy cows (FIGS. 14A-14E).

A. IsdA specific IgG serum titers of IsdA-CTA$_2$/B vaccinated cows (2472, 2340, 2319) and IsdA control vaccinated cows (2403, 2299, 2296).

Titers were calculated as the highest dilution 0.2 O.D. above background and were reported as a ratio with Day 0. Combined titers of IsdA-CTA$_2$/B vaccinated cows were significant over IsdA control vaccinated cows on day 49 (**Student's t-test, p-0.003)

B. IsdA specific IgG milk titers of IsdA-CTA2/B vaccinated cows (2472, 2340, 2319) and IsdA control vaccinated cows (2403, 2299, 2296).

Titers were calculated as the highest dilution 0.2 O.D. above background and are reported as a ratio with Day 0. Combined titers of IsdA-CTA$_2$/B vaccinated cows were significant over IsdA control vaccinated cows on days 14, 28, and 49 (*Student's t-test, p<0.05).

C. IsdA-specific IgA in milk from IsdA-CTA2/B vaccinated cows and IsdA vaccinated cows.

Levels were reported as the ratio of IsdA specific IgA over total IgA after the subtraction of Day 0 at a milk dilution of 1:8. No significant differences were detected between IsdA-CTA$_2$/B vaccinated cows and IsdA control vaccinated cows.

D. IsdA-specific IgA in nasal secretions from IsdA-CTA$_2$/B vaccinated cows and IsdA vaccinated cows.

Levels were reported as the ratio of IsdA specific IgA over total IgA after the subtraction of Day 0 at a nasal wash dilution of 1:8. No significant differences were detected between IsdA-CTA2/B vaccinated cows and IsdA control vaccinated cows.

E. Somatic cell counts throughout the study of IsdA-CTA$_2$/B vaccinated cows and IsdA vaccinated cows. No significant differences were detected between IsdA-CTA$_2$/B vaccinated cows and IsdA control vaccinated cows.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of generating an immune response to *Staphylococcus aureus* in a mammal comprising administering to the mammal a composition comprising a chimeric protein comprising a cholera toxin A2 having the amino acid sequence of SEQ ID NO: 2 or an amino acid sequence that is at least 90% identical to SEQ ID NO: 2, a cholera toxin B having the amino acid sequence of SEQ ID NO: 3 or an amino acid sequence that is at least 90% identical to SEQ ID NO: 3, and an isolated *Staphylococcus aureus*-specific clumping factor A (ClfA) polypeptide consisting of amino acid residues 24-300 as set forth within the amino acid sequence of SEQ ID NO: 24.

2. The method of claim 1, wherein the chimeric protein comprises the amino acid sequence of SEQ ID NO: 24.

3. The method of claim 1, wherein the chimeric protein is a single polypeptide.

4. The method of claim 1, wherein the chimeric protein is a fusion protein.

5. The method of claim 1, wherein the mammal is a cow.

6. The method of claim 1, wherein the mammal is a human and the chimeric protein is purified.

7. The method of claim 1, wherein the administration of the composition is selected from the group consisting of intranasal administration, subcutaneous administration, intramuscular administration, and any combination thereof.

* * * * *

SEQUENCE LISTING

<160> NUMBER OF SEQ ID NOS: 26

<210> SEQ ID NO 1
<211> LENGTH: 193
<212> TYPE: PRT
<213> ORGANISM: Vibrio cholerae

<400> SEQUENCE: 1

Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp

```
            20                  25                  30
Arg Gly Thr Gln Met Asn Ile Asn Leu Tyr Asp His Ala Arg Gly Thr
            35                  40                  45

Gln Thr Gly Phe Val Arg His Asp Asp Gly Tyr Val Ser Thr Ser Ile
        50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
            115                 120                 125

Arg Val His Phe Gly Val Leu Asp Glu Gln Leu His Arg Asn Arg Gly
            130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser

<210> SEQ ID NO 2
<211> LENGTH: 47
<212> TYPE: PRT
<213> ORGANISM: Vibrio cholerae

<400> SEQUENCE: 2

Ser Met Ser Asn Thr Ser Asp Glu Lys Thr Gln Ser Leu Gly Val Lys
1               5                   10                  15

Phe Leu Asp Glu Tyr Gln Ser Lys Val Lys Arg Gln Ile Phe Ser Gly
                20                  25                  30

Tyr Gln Ser Asp Ile Asp Thr His Asn Arg Ile Lys Asp Glu Leu
            35                  40                  45

<210> SEQ ID NO 3
<211> LENGTH: 103
<212> TYPE: PRT
<213> ORGANISM: Vibrio cholerae

<400> SEQUENCE: 3

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
            35                  40                  45

Gln Val Glu Val Pro Gly Ser Gln His Ile Asp Ser Gln Lys Lys Ala
        50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

```
<210> SEQ ID NO 4
<211> LENGTH: 273
<212> TYPE: PRT
<213> ORGANISM: Staphylococcus aureus

<400> SEQUENCE: 4
```

| | | | | | | | | | | | | | | | |
|---|---|---|---|---|---|---|---|---|---|---|---|---|---|---|---|
| Ala | Thr | Glu | Ala | Thr | Asn | Ala | Thr | Asn | Asn | Gln | Ser | Thr | Gln | Val | Ser |
| 1 | | | | 5 | | | | | 10 | | | | | 15 | |
| Gln | Ala | Thr | Ser | Gln | Pro | Ile | Asn | Phe | Gln | Val | Gln | Lys | Asp | Gly | Ser |
| | | | 20 | | | | | 25 | | | | | 30 | | |
| Ser | Glu | Lys | Ser | His | Met | Asp | Asp | Tyr | Met | Gln | His | Pro | Gly | Lys | Val |
| | | 35 | | | | | 40 | | | | | 45 | | | |
| Ile | Lys | Gln | Asn | Asn | Lys | Tyr | Tyr | Phe | Gln | Ala | Val | Leu | Asn | Asn | Ala |
| | 50 | | | | | 55 | | | | | 60 | | | | |
| Ser | Phe | Trp | Lys | Glu | Tyr | Lys | Phe | Tyr | Asn | Ala | Asn | Gln | Glu | Leu |
| 65 | | | | | 70 | | | | | 75 | | | | | 80 |
| Ala | Thr | Thr | Val | Val | Asn | Asp | Asp | Lys | Lys | Ala | Asp | Thr | Arg | Thr | Ile |
| | | | | 85 | | | | | 90 | | | | | 95 | |
| Asn | Val | Ala | Val | Glu | Pro | Gly | Tyr | Lys | Ser | Leu | Thr | Thr | Lys | Val | His |
| | | | 100 | | | | | 105 | | | | | 110 | | |
| Ile | Val | Val | Pro | Gln | Ile | Asn | Tyr | Asn | His | Arg | Tyr | Thr | Thr | His | Leu |
| | | 115 | | | | | 120 | | | | | 125 | | | |
| Glu | Phe | Glu | Lys | Ala | Ile | Pro | Thr | Leu | Ala | Asp | Ala | Ala | Lys | Pro | Asn |
| | 130 | | | | | 135 | | | | | 140 | | | | |
| Asn | Val | Lys | Pro | Val | Gln | Pro | Lys | Pro | Ala | Gln | Pro | Lys | Thr | Pro | Thr |
| 145 | | | | | 150 | | | | | 155 | | | | | 160 |
| Glu | Gln | Thr | Lys | Pro | Val | Gln | Pro | Lys | Val | Glu | Lys | Val | Lys | Pro | Ala |
| | | | | 165 | | | | | 170 | | | | | 175 | |
| Val | Thr | Ala | Pro | Ser | Lys | Asn | Glu | Asn | Arg | Gln | Thr | Thr | Lys | Val | Val |
| | | | 180 | | | | | 185 | | | | | 190 | | |
| Ser | Ser | Glu | Ala | Thr | Lys | Asp | Gln | Ser | Gln | Thr | Gln | Ser | Ala | Arg | Thr |
| | | 195 | | | | | 200 | | | | | 205 | | | |
| Val | Lys | Thr | Thr | Gln | Thr | Ala | Gln | Asp | Gln | Asn | Lys | Val | Gln | Thr | Pro |
| | 210 | | | | | 215 | | | | | 220 | | | | |
| Val | Lys | Asp | Val | Ala | Thr | Ala | Lys | Ser | Glu | Ser | Asn | Asn | Gln | Ala | Val |
| 225 | | | | | 230 | | | | | 235 | | | | | 240 |
| Ser | Asp | Asn | Lys | Ser | Gln | Gln | Thr | Asn | Lys | Val | Thr | Lys | Gln | Asn | Glu |
| | | | | 245 | | | | | 250 | | | | | 255 | |
| Val | His | Lys | Gln | Gly | Pro | Ser | Lys | Asp | Ser | Lys | Ala | Lys | Glu | Leu | Pro |
| | | | 260 | | | | | 265 | | | | | 270 | | |
| Lys | | | | | | | | | | | | | | | |

```
<210> SEQ ID NO 5
<211> LENGTH: 423
<212> TYPE: PRT
<213> ORGANISM: Artificial Sequence
<220> FEATURE:
<223> OTHER INFORMATION: Description of Artificial Sequence: Synthetic
      chimeric protein IsdA-CTA2/B polypeptide

<400> SEQUENCE: 5
```

| | | | | | | | | | | | | | | | |
|---|---|---|---|---|---|---|---|---|---|---|---|---|---|---|---|
| Ala | Thr | Glu | Ala | Thr | Asn | Ala |

Ser Glu Lys Ser His Met Asp Asp Tyr Met Gln His Pro Gly Lys Val
             35                  40                  45

Ile Lys Gln Asn Asn Lys Tyr Tyr Phe Gln Ala Val Leu Asn Asn Ala
 50                  55                  60

Ser Phe Trp Lys Glu Tyr Lys Phe Tyr Asn Ala Asn Asn Gln Glu Leu
 65                  70                  75                  80

Ala Thr Thr Val Val Asn Asp Lys Lys Ala Asp Thr Arg Thr Ile
                 85                  90                  95

Asn Val Ala Val Glu Pro Gly Tyr Lys Ser Leu Thr Thr Lys Val His
                100                 105                 110

Ile Val Val Pro Gln Ile Asn Tyr Asn His Arg Tyr Thr Thr His Leu
                115                 120                 125

Glu Phe Glu Lys Ala Ile Pro Thr Leu Ala Asp Ala Ala Lys Pro Asn
            130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
            210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ser Met Ser Asn Thr Ser Asp Glu Lys Thr Gln Ser Leu Gly Val
            275                 280                 285

Lys Phe Leu Asp Glu Tyr Gln Ser Lys Val Lys Arg Gln Ile Phe Ser
            290                 295                 300

Gly Tyr Gln Ser Asp Ile Asp Thr His Asn Arg Ile Lys Asp Glu Leu
305                 310                 315                 320

Thr Pro Gln Asn Ile Thr Asp Leu Cys Ala Glu Tyr His Asn Thr Gln
                325                 330                 335

Ile His Thr Leu Asn Asp Lys Ile Phe Ser Tyr Thr Glu Ser Leu Ala
            340                 345                 350

Gly Lys Arg Glu Met Ala Ile Ile Thr Phe Lys Asn Gly Ala Thr Phe
        355                 360                 365

Gln Val Glu Val Pro Gly Ser Gln His Ile Asp Ser Gln Lys Lys Ala
            370                 375                 380

Ile Glu Arg Met Lys Asp Thr Leu Arg Ile Ala Tyr Leu Thr Glu Ala
385                 390                 395                 400

Lys Val Glu Lys Leu Cys Val Trp Asn Asn Lys Thr Pro His Ala Ile
                405                 410                 415

Ala Ala Ile Ser Met Ala Asn
            420

<210> SEQ ID NO 6
<211> LENGTH: 320
<212> TYPE: PRT

<213> ORGANISM: Artificial Sequence
<220> FEATURE:
<223> OTHER INFORMATION: Description of Artificial Sequence: Synthetic chimeric protein Isda-CTA2 polypeptide

<400> SEQUENCE: 6

| Ala | Thr | Glu | Ala | Thr | Asn | Ala | Thr | Asn | Asn | Gln | Ser | Thr | Gln | Val | Ser |
|---

```
            20                  25                  30
Arg Gly Thr Gln Met Asn Ile Asn Leu Tyr Asp His Ala Arg Gly Thr
            35                  40                  45

Gln Thr Gly Phe Val Arg Tyr Asp Asp Gly Tyr Val Ser Thr Ser Leu
        50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
            115                 120                 125

Arg Val Asn Phe Gly Val Ile Asp Glu Arg Leu His Arg Asn Arg Glu
            130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr

<210> SEQ ID NO 8
<211> LENGTH: 47
<212> TYPE: PRT
<213> ORGANISM: Escherichia coli

<400> SEQUENCE: 8

Ile Thr Gly Asp Thr Cys Asn Glu Glu Thr Gln Asn Leu Ser Thr Ile
1               5                   10                  15

Tyr Leu Arg Lys Tyr Gln Ser Lys Val Lys Arg Gln Ile Phe Ser Asp
            20                  25                  30

Tyr Gln Ser Glu Val Asp Ile Tyr Asn Arg Ile Arg Asn Glu Leu
        35                  40                  45

<210> SEQ ID NO 9
<211> LENGTH: 103
<212> TYPE: PRT
<213> ORGANISM: Escherichia coli

<400> SEQUENCE: 9

Ala Pro Gln Ser Ile Thr Glu Leu Cys Ser Glu Tyr His Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100
```

<210> SEQ ID NO 10
<211> LENGTH: 423
<212> TYPE: PRT
<213> ORGANISM: Artificial Sequence
<220> FEATURE:
<223> OTHER INFORMATION: Description of Artificial Sequence: Synthetic chimeric protein IsdA-LTA2/B polypeptide

<400> SEQUENCE: 10

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ile Thr Gly Asp Thr Cys Asn Glu Glu Thr Gln Asn Leu Ser Thr
        275                 280                 285

Ile Tyr Leu Arg Lys Tyr Gln Ser Lys Val Lys Arg Gln Ile Phe Ser
    290                 295                 300

Asp Tyr Gln Ser Glu Val Asp Ile Tyr Asn Arg Ile Arg Asn Glu Leu
305                 310                 315                 320

Ala Pro Gln Ser Ile Thr Glu Leu Cys Ser Glu Tyr His Asn Thr Gln
                325                 330                 335

Ile Tyr Thr Ile Asn Asp Lys Ile Leu Ser Tyr Thr Glu Ser Met Ala
            340                 345                 350

Gly Lys Arg Glu Met Val Ile Ile Thr Phe Lys Ser Gly Ala Thr Phe
```

```
                355                 360                 365
Gln Val Glu Val Pro Gly Ser Gln His Ile Asp Ser Gln Lys Lys Ala
    370                 375                 380

Ile Glu Arg Met Lys Asp Thr Leu Arg Ile Thr Tyr Leu Thr Glu Thr
385                 390                 395                 400

Lys Ile Asp Lys Leu Cys Val Trp Asn Asn Lys Thr Pro Asn Ser Ile
                405                 410                 415

Ala Ala Ile Ser Met Glu Asn
            420

<210> SEQ ID NO 11
<211> LENGTH: 320
<212> TYPE: PRT
<213> ORGANISM: Artificial Sequence
<220> FEATURE:
<223> OTHER INFORMATION: Description of Artificial Sequence: Synthetic
      chimeric protein IsdA-LTA2 polypeptide

<400> SEQUENCE: 11

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ile Thr Gly Asp Thr Cys Asn Glu Glu Thr Gln Asn Leu Ser Thr
        275                 280                 285
```

```
Ile Tyr Leu Arg Lys Tyr Gln Ser Lys Val Lys Arg Gln Ile Phe Ser
    290                 295                 300

Asp Tyr Gln Ser Glu Val Asp Ile Tyr Asn Arg Ile Arg Asn Glu Leu
305                 310                 315                 320

<210> SEQ ID NO 12
<211> LENGTH: 250
<212> TYPE: PRT
<213> ORGANISM: Escherichia coli

<400> SEQUENCE: 12

Glu Phe Thr Leu Asp Phe Ser Thr Ala Lys Thr Tyr Val Asp Ser Leu
1               5                   10                  15

Asn Val Ile Arg Ser Ala Ile Gly Thr Pro Leu Gln Thr Ile Ser Ser
            20                  25                  30

Gly Gly Thr Ser Leu Leu Met Ile Asp Ser Gly Thr Gly Asp Asn Leu
        35                  40                  45

Phe Ala Val Asp Val Arg Gly Ile Asp Pro Glu Glu Gly Arg Phe Asn
    50                  55                  60

Asn Leu Arg Leu Ile Val Glu Arg Asn Asn Leu Tyr Val Thr Gly Phe
65                  70                  75                  80

Val Asn Arg Thr Asn Asn Val Phe Tyr Arg Phe Ala Asp Phe Ser His
                85                  90                  95

Val Thr Phe Pro Gly Thr Thr Ala Val Thr Leu Ser Gly Asp Ser Ser
            100                 105                 110

Tyr Thr Thr Leu Gln Arg Val Ala Gly Ile Ser Arg Thr Gly Met Gln
        115                 120                 125

Ile Asn Arg His Ser Leu Thr Thr Ser Tyr Leu Asp Leu Met Ser His
    130                 135                 140

Ser Gly Thr Ser Leu Thr Gln Ser Val Ala Arg Ala Met Leu Arg Phe
145                 150                 155                 160

Val Thr Val Thr Ala Glu Ala Leu Arg Phe Arg Gln Ile Gln Arg Gly
                165                 170                 175

Phe Arg Thr Thr Leu Asp Asp Leu Ser Gly Arg Ser Tyr Val Met Thr
            180                 185                 190

Ala Glu Asp Val Asp Leu Thr Leu Asn Trp Gly Arg Leu Ser Ser Val
        195                 200                 205

Leu Pro Asp Tyr His Gly Gln Asp Ser Val Arg Val Gly Arg Ile Ser
    210                 215                 220

Phe Gly Ser Ile Asn Ala Ile Leu Gly Ser Val Ala Leu Ile Leu Asn
225                 230                 235                 240

Cys His His His Ala Ser Arg Val Ala Arg
                245                 250

<210> SEQ ID NO 13
<211> LENGTH: 42
<212> TYPE: PRT
<213> ORGANISM: Escherichia coli

<400> SEQUENCE: 13

Met Ala Ser Asp Glu Phe Pro Ser Met Cys Pro Ala Asp Gly Arg Val
1               5                   10                  15

Arg Gly Ile Thr His Asn Lys Ile Leu Trp Asp Ser Ser Thr Leu Gly
            20                  25                  30

Ala Ile Leu Met Arg Arg Thr Ile Ser Ser
        35                  40
```

<210> SEQ ID NO 14
<211> LENGTH: 69
<212> TYPE: PRT
<213> ORGANISM: Escherichia coli

<400> SEQUENCE: 14

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Ser Ala Gln Ile Thr Gly Met
        35                  40                  45

Thr Val Thr Ile Lys Thr Asn Ala Cys His Asn Gly Gly Phe Ser
50                  55                  60

Glu Val Ile Phe Arg
65

<210> SEQ ID NO 15
<211> LENGTH: 384
<212> TYPE: PRT
<213> ORGANISM: Artificial Sequence
<220> FEATURE:
<223> OTHER INFORMATION: Description of Artificial Sequence: Synthetic
      chimeric protein IsdA-STA2/B polypeptide

<400> SEQUENCE: 15

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Leu Ser Glu Ser Asn Asn Gln Ala Val
225                 230                 235                 240

```
Ser Asp Asn Lys Ser Gln Gln Thr Asn Lys Val Thr Lys Gln Asn Glu
            245                 250                 255

Val His Lys Gln Gly Pro Ser Lys Asp Ser Lys Ala Lys Glu Leu Pro
        260                 265                 270

Lys Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
        290                 295                 300

Gly Ala Ile Leu Met Arg Arg Thr Ile Ser Ser Thr Pro Asp Cys Val
305                 310                 315                 320

Thr Gly Lys Val Glu Tyr Thr Lys Tyr Asn Asp Asp Thr Phe Thr
                325                 330                 335

Val Lys Val Gly Asp Lys Glu Leu Phe Thr Asn Arg Trp Asn Leu Gln
        340                 345                 350

Ser Leu Leu Leu Ser Ala Gln Ile Thr Gly Met Thr Val Thr Ile Lys
        355                 360                 365

Thr Asn Ala Cys His Asn Gly Gly Phe Ser Glu Val Ile Phe Arg
        370                 375                 380

<210> SEQ ID NO 16
<211> LENGTH: 315
<212> TYPE: PRT
<213> ORGANISM: Artificial Sequence
<220> FEATURE:
<223> OTHER INFORMATION: Description of Artificial Sequence: Synthetic
      chimeric protein IsdA-STA2 polypeptide

<400> SEQUENCE: 16

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220
```

```
Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Leu Asp Ser Lys Ala Lys Glu Leu Pro
            260                 265                 270

Lys Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      5' SphI PCR primer

<400> SEQUENCE: 17
gctactggca tgcggcaaca gaagctacga ac                                    32

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      3' ClaI primer

<400> SEQUENCE: 18
gtgcatgatc gattttggta attctttagc                                       30

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      5' BamHI primer

<400> SEQUENCE: 19
gctactggat ccgcggcaac agaagctacg aac                                   33

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      5' BamHI alternative primer

<400> SEQUENCE: 20
gtgcataagc tttcaagttt ttggtaattc tttagc                                36

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      3' HindIII primer
```

<400> SEQUENCE: 21
gtgcatgatc gattttggta attctttagc                                                                30

<210> SEQ ID NO 22
<211> LENGTH: 367
<212> TYPE: PRT
<213> ORGANISM: Artificial Sequence
<220> FEATURE:
<223> OTHER INFORMATION: Description of Artificial Sequence: Synthetic
      chimeric protein IsdB-CTA2 polypeptide

<400> SEQUENCE: 22

Met Ser Phe Lys Lys Ile Ile Lys Ala Phe Val Ile Met Ala Ala Leu
1               5                   10                  15

Val Ser Val Gln Ala His Ala Ala Glu Glu Thr Gly Gly Thr Asn Thr
            20                  25                  30

Glu Ala Gln Pro Lys Thr Glu Ala Val Ala Ser Pro Thr Thr Thr Ser
        35                  40                  45

Glu Lys Ala Pro Glu Thr Lys Pro Val Ala Asn Ala Val Ser Val Ser
    50                  55                  60

Asn Lys Glu Val Glu Ala Pro Thr Ser Glu Thr Lys Glu Ala Lys Glu
65                  70                  75                  80

Val Lys Glu Val Lys Ala Pro Lys Glu Thr Lys Glu Val Lys Pro Ala
                85                  90                  95

Ala Lys Ala Thr Asn Asn Thr Tyr Pro Ile Leu Asn Gln Glu Leu Arg
            100                 105                 110

Glu Ala Ile Lys Asn Pro Ala Ile Lys Asp Lys Asp His Ser Ala Pro
        115                 120                 125

Asn Ser Arg Pro Ile Asp Phe Glu Met Lys Lys Asp Gly Thr Gln
130                 135                 140

Gln Phe Tyr His Tyr Ala Ser Ser Val Lys Pro Ala Arg Val Ile Phe
145                 150                 155                 160

Thr Asp Ser Lys Pro Glu Ile Glu Leu Gly Leu Gln Ser Gly Gln Phe
                165                 170                 175

Trp Arg Lys Phe Glu Val Tyr Glu Gly Asp Lys Lys Leu Pro Ile Lys
            180                 185                 190

Leu Val Ser Tyr Asp Thr Val Lys Asp Tyr Ala Tyr Ile Arg Phe Ser
        195                 200                 205

Val Ser Asn Gly Thr Lys Ala Val Lys Ile Val Ser Ser Thr His Phe
    210                 215                 220

Asn Asn Lys Glu Glu Lys Tyr Asp Tyr Thr Leu Met Glu Phe Ala Gln
225                 230                 235                 240

Pro Ile Tyr Asn Ser Ala Asp Lys Phe Lys Thr Glu Glu Asp Tyr Lys
                245                 250                 255

Ala Glu Lys Leu Leu Ala Pro Tyr Lys Lys Ala Lys Thr Leu Glu Arg
            260                 265                 270

Gln Val Tyr Glu Leu Asn Lys Ile Gln Asp Lys Leu Pro Glu Lys Leu
        275                 280                 285

Lys Ala Glu Tyr Lys Lys Leu Glu Asp Thr Lys Lys Ala Leu Asp
    290                 295                 300

Glu Gln Val Lys Ser Ala Ile Thr Glu Phe Gln Asn Val Gln Pro Thr
305                 310                 315                 320

Ser Met Ser Asn Thr Ser Asp Glu Lys Thr Gln Ser Leu Gly Val Lys
                325                 330                 335

```
Phe Leu Asp Glu Tyr Gln Ser Lys Val Lys Arg Gln Ile Phe Ser Gly
            340                 345                 350

Tyr Gln Ser Asp Ile Asp Thr His Asn Arg Ile Lys Asp Glu Leu
        355                 360                 365

<210> SEQ ID NO 23
<211> LENGTH: 645
<212> TYPE: PRT
<213> ORGANISM: Staphylococcus aureus

<400> SEQUENCE: 23

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Glu Glu Thr Gly Gly Thr
            35                  40                  45

Asn Thr Glu Ala Gln Pro Lys Thr Glu Ala Val Ala Ser Pro Thr Thr
50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350
```

```
Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 24
<211> LENGTH: 347
<212> TYPE: PRT
<213> ORGANISM: Artificial Sequence
<220> FEATURE:
<223> OTHER INFORMATION: Description of Artificial Sequence: Synthetic
      chimeric protein ClfA-CTA2 polypeptide

<400> SEQUENCE: 24

Met Ser Phe Lys Lys Ile Ile Lys Ala Phe Val Ile Met Ala Ala Leu
1               5                   10                  15

Val Ser Val Gln Ala His Ala Gly Val Thr Ser Thr Ala Lys Val Pro
            20                  25                  30

Pro Ile Met Ala Gly Asp Gln Val Leu Ala Asn Gly Val Ile Asp Ser
        35                  40                  45

Asp Gly Asn Val Ile Tyr Thr Phe Thr Asp Tyr Val Asn Thr Lys Asp
```

```
                    50                  55                  60
Asp Val Lys Ala Thr Leu Thr Met Pro Ala Tyr Ile Asp Pro Glu Asn
 65                  70                  75                  80

Val Lys Lys Thr Gly Asn Val Thr Leu Ala Thr Gly Ile Gly Ser Thr
                 85                  90                  95

Thr Ala Asn Lys Thr Val Leu Val Asp Tyr Glu Lys Tyr Gly Lys Phe
                100                 105                 110

Tyr Asn Leu Ser Ile Lys Gly Thr Ile Asp Gln Ile Asp Lys Thr Asn
                115                 120                 125

Asn Thr Tyr Arg Gln Thr Ile Tyr Val Asn Pro Ser Gly Asp Asn Val
            130                 135                 140

Ile Ala Pro Val Leu Thr Gly Asn Leu Lys Pro Asn Thr Asp Ser Asn
145                 150                 155                 160

Ala Leu Ile Asp Gln Gln Asn Thr Ser Ile Lys Val Tyr Lys Val Asp
                165                 170                 175

Asn Ala Ala Asp Leu Ser Glu Ser Tyr Phe Val Asn Pro Glu Asn Phe
            180                 185                 190

Glu Asp Val Thr Asn Ser Val Asn Ile Thr Phe Pro Asn Pro Asn Gln
                195                 200                 205

Tyr Lys Val Glu Phe Asn Thr Pro Asp Asp Gln Ile Thr Thr Pro Tyr
            210                 215                 220

Ile Val Val Asn Gly His Ile Asp Pro Asn Ser Lys Gly Asp Leu
225                 230                 235                 240

Ala Leu Arg Ser Thr Leu Tyr Gly Tyr Asn Ser Asn Ile Ile Trp Arg
                245                 250                 255

Ser Met Ser Trp Asp Asn Glu Val Ala Phe Asn Asn Gly Ser Gly Ser
            260                 265                 270

Gly Asp Gly Ile Asp Lys Pro Val Pro Glu Gln Pro Asp Glu Pro
            275                 280                 285

Gly Glu Ile Glu Pro Ile Pro Ser Arg Ser Thr Val Ser Met Ser Asn
            290                 295                 300

Thr Ser Asp Glu Lys Thr Gln Ser Leu Gly Val Lys Phe Leu Asp Glu
305                 310                 315                 320

Tyr Gln Ser Lys Val Lys Arg Gln Ile Phe Ser Gly Tyr Gln Ser Asp
                325                 330                 335

Ile Asp Thr His Asn Arg Ile Lys Asp Glu Leu
            340                 345

<210> SEQ ID NO 25
<211> LENGTH: 933
<212> TYPE: PRT
<213> ORGANISM: Staphylococcus aureus

<400> SEQUENCE: 25

Met Asn Met Lys Lys Lys Glu Lys His Ala Ile Arg Lys Lys Ser Ile
 1               5                  10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
         50                  55                  60

Ala Pro Lys Thr Asp Asp Thr Asn Val Ser Asp Thr Lys Thr Ser Ser
 65                  70                  75                  80
```

-continued

```
Asn Thr Asn Asn Gly Glu Thr Ser Val Ala Gln Asn Pro Ala Gln Gln
                 85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
            115                 120                 125

Ala Thr Thr Gln Ser Ser Asn Thr Asn Ala Glu Glu Leu Val Asn Gln
        130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
```

```
              500                 505                 510
Asn Ser Asn Ile Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
        530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
        595                 600                 605

Ser Asp Ser Ala Ser Asp Ser Asp Ser Ala Ser Asp Ser Asp Ser Asp
    610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                645                 650                 655

Ser Asp Ser Asp Ser Asp Ser Asp Ser Asp Ser Asp Ser Asp Ser Asp
            660                 665                 670

Ser Asp Ser Asp Ser Asp Ser Asp Ser Asp Ser Asp Ser Asp Ser Asp
        675                 680                 685

Ser Asp Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
        755                 760                 765

Ser Asp Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
                805                 810                 815

Ser Asp Ser Asp Ser Asp Ser Asp Ser Asp Ser Asp Ser Asp Ser Asp
            820                 825                 830

Ser Asp Ser Asp Ser Ala Ser Asp Ser Asp Ser Gly Ser Asp Ser Asp
        835                 840                 845

Ser Ser Ser Asp Ser Asp Ser Glu Ser Asp Ser Asn Ser Asp Ser Glu
    850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
            900                 905                 910

Leu Leu Ala Ser Ile Gly Ser Leu Leu Leu Phe Arg Arg Lys Lys Glu
        915                 920                 925
```

```
Asn Lys Asp Lys Lys
    930

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5
```